United States Patent
Huber et al.

(10) Patent No.: US 9,538,383 B2
(45) Date of Patent: *Jan. 3, 2017

(54) INTERFACE FOR ACCESS MANAGEMENT OF FEMTO CELL COVERAGE

(71) Applicant: AT&T Mobility II LLC, Atlanta, GA (US)

(72) Inventors: Kurt Donald Huber, Coral Springs, FL (US); Judson John Flynn, Decatur, GA (US); William Gordon Mansfield, Sugar Hill, GA (US)

(73) Assignee: AT&T MOBILITY II LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/831,013

(22) Filed: Aug. 20, 2015

(65) Prior Publication Data

US 2015/0373547 A1 Dec. 24, 2015

Related U.S. Application Data

(63) Continuation of application No. 13/917,153, filed on Jun. 13, 2013, now Pat. No. 9,155,022, which is a (Continued)

(51) Int. Cl.
*G06F 7/04* (2006.01)
*H04W 12/08* (2009.01)
(Continued)

(52) U.S. Cl.
CPC ......... *H04W 12/08* (2013.01); *G06Q 20/1235* (2013.01); *G06Q 20/32* (2013.01);
(Continued)

(58) Field of Classification Search
CPC ...... H04L 63/08; G06F 21/6218; G06F 21/30; G06F 21/44
(Continued)

(56) References Cited

U.S. PATENT DOCUMENTS 5,745,559 A 4/1998 Weir
5,864,764 A 1/1999 Thro et al.
(Continued)

FOREIGN PATENT DOCUMENTS

CN 1429005 A 7/2003
CN 101017554 8/2007
(Continued)

OTHER PUBLICATIONS

International Search Report and Written Opinion dated Oct. 27, 2009 for PCT Application Serial No. PCT/US2009/043861, 14 Pages.
(Continued)

*Primary Examiner* — Anthony Brown
(74) *Attorney, Agent, or Firm* — Amin, Turocy & Watson, LLP

(57) ABSTRACT

Access to femto cell service is managed through access control list(s), or "white list(s)." Such white list(s) can be configured via a networked interface which facilitates access management to a femto cell. White list(s) includes a set of subscriber station(s) identifier numbers, codes or tokens, and can also include additional fields for femto cell access management based on desired complexity. Various interfaces and user profiles are associated with granting different levels of access to requesting UEs.

20 Claims, 18 Drawing Sheets

Related U.S. Application Data continuation of application No. 12/276,002, filed on Nov. 21, 2008, now Pat. No. 8,490,156.

(60) Provisional application No. 61/052,813, filed on May 13, 2008.

(51) Int. Cl.

| | |
|---|---|
| *H04W 4/12* | (2009.01) |
| *H04W 48/04* | (2009.01) |
| *G06Q 20/12* | (2012.01) |
| *G06Q 20/32* | (2012.01) |
| *G06Q 20/38* | (2012.01) |
| *G06Q 20/40* | (2012.01) |
| *G06Q 30/02* | (2012.01) |
| *G06Q 30/06* | (2012.01) |
| *H04L 29/06* | (2006.01) |
| *H04W 48/08* | (2009.01) |
| *H04W 48/20* | (2009.01) |
| *H04W 48/16* | (2009.01) |
| *H04W 4/02* | (2009.01) |
| *H04L 12/24* | (2006.01) |
| *H04W 8/22* | (2009.01) |
| *H04W 88/08* | (2009.01) |
| *H04W 8/20* | (2009.01) |
| *H04W 48/02* | (2009.01) |
| *H04W 64/00* | (2009.01) |
| *H04W 68/02* | (2009.01) |
| *H04L 5/00* | (2006.01) |
| *H04W 4/04* | (2009.01) |
| *H04W 84/04* | (2009.01) |

(52) U.S. Cl.
CPC ....... *G06Q 20/322* (2013.01); *G06Q 20/3223* (2013.01); *G06Q 20/387* (2013.01); *G06Q 20/405* (2013.01); *G06Q 30/02* (2013.01); *G06Q 30/0222* (2013.01); *G06Q 30/0261* (2013.01); *G06Q 30/0601* (2013.01); *H04L 5/0048* (2013.01); *H04L 41/0803* (2013.01); *H04L 63/101* (2013.01); *H04L 63/108* (2013.01); *H04W 4/02* (2013.01); *H04W 4/023* (2013.01); *H04W 4/027* (2013.01); *H04W 4/046* (2013.01); *H04W 4/12* (2013.01); *H04W 8/20* (2013.01); *H04W 8/22* (2013.01); *H04W 48/02* (2013.01); *H04W 48/04* (2013.01); *H04W 48/08* (2013.01); *H04W 48/16* (2013.01); *H04W 48/20* (2013.01); *H04W 64/006* (2013.01); *H04W 68/02* (2013.01); *H04W 88/08* (2013.01); *H04L 63/0876* (2013.01); *H04L 2209/80* (2013.01); *H04W 84/045* (2013.01)

(58) Field of Classification Search
USPC .......................................................... 726/2
See application file for complete search history.

(56) References Cited

U.S. PATENT DOCUMENTS

| | | | |
|---|---|---|---|
| 5,956,715 A | 9/1999 | Glasser et al. |
| 6,052,594 A | 4/2000 | Chuang et al. |
| 6,151,505 A | 11/2000 | Larkins |
| 6,208,659 B1 | 3/2001 | Govindarajan et al. |
| 6,219,786 B1 | 4/2001 | Cunningham et al. |
| 6,256,504 B1 | 7/2001 | Tell et al. |
| 6,266,537 B1 | 7/2001 | Kashitani et al. |
| 6,295,454 B1 | 9/2001 | Havinis et al. |
| 6,363,261 B1 | 3/2002 | Raghavan |
| 6,483,852 B1 | 11/2002 | Jacquet et al. |
| 6,484,096 B2 | 11/2002 | Wong |
| 6,512,478 B1 | 1/2003 | Chien |
| 6,710,651 B2 | 3/2004 | Forrester |
| 6,718,023 B1 | 4/2004 | Zolotov |
| 6,768,722 B1 | 7/2004 | Katseff et al. |
| 7,080,139 B1 | 7/2006 | Briggs et al. |
| 7,142,861 B2 | 11/2006 | Murai |
| 7,146,153 B2 | 12/2006 | Russell |
| 7,155,526 B2 | 12/2006 | Chaudhary et al. |
| 7,209,739 B1 | 4/2007 | Narayanabhatla |
| 7,218,912 B2 | 5/2007 | Erskine et al. |
| 7,277,410 B2 | 10/2007 | Horneman |
| 7,317,931 B2 | 1/2008 | Guo |
| 7,370,356 B1 | 5/2008 | Guo |
| 7,437,755 B2 | 10/2008 | Farino et al. |
| 7,493,390 B2 | 2/2009 | Bobde et al. |
| 7,496,383 B2 | 2/2009 | Kurata |
| 7,509,124 B2 | 3/2009 | O'Neil |
| 7,516,219 B2 | 4/2009 | Moghaddam et al. |
| 7,551,574 B1 | 6/2009 | Peden et al. |
| 7,558,251 B1 | 7/2009 | Huang et al. |
| 7,574,731 B2 | 8/2009 | Fascenda et al. |
| 7,613,444 B2 | 11/2009 | Lindqvist et al. |
| 7,614,078 B1 | 11/2009 | Stieglitz et al. |
| 7,623,857 B1 | 11/2009 | O'Neil |
| 7,633,910 B2 | 12/2009 | Zhun et al. |
| 7,751,826 B2 | 7/2010 | Gardner |
| 7,761,526 B2 | 7/2010 | Pounds et al. |
| 7,768,983 B2 | 8/2010 | Nylander et al. |
| 7,853,265 B1 | 12/2010 | Ahmad et al. |
| 7,885,644 B2 | 2/2011 | Gallagher et al. |
| 7,929,537 B2 | 4/2011 | Vasudevan et al. |
| 7,929,970 B1 | 4/2011 | Gunasekara |
| 7,941,144 B2 | 5/2011 | Nylander et al. |
| 7,995,994 B2 | 8/2011 | Khetawat et al. |
| 8,041,335 B2 | 10/2011 | Khetawat et al. |
| 8,064,909 B2 | 11/2011 | Spinelli et al. |
| 8,103,285 B2 | 1/2012 | Kalhan et al. |
| 8,108,923 B1 | 1/2012 | Satish et al. |
| 8,265,685 B2 | 9/2012 | Vikberg et al. |
| 8,437,745 B2 | 5/2013 | Theppasandra et al. |
| 8,509,778 B2 | 8/2013 | Buchmayer et al. |
| 8,510,801 B2 | 8/2013 | Majmundar et al. |
| 8,522,312 B2 | 8/2013 | Huber et al. |
| 8,743,776 B2 | 6/2014 | Gurajala et al. |
| 8,774,155 B2 | 7/2014 | Passarella et al. |
| 8,856,878 B2 | 10/2014 | Wohlert |
| 2002/0044639 A1 | 4/2002 | Shioda et al. |
| 2002/0077115 A1 | 6/2002 | Ruutu et al. |
| 2002/0098837 A1 | 7/2002 | Ferrario et al. |
| 2002/0107018 A1 | 8/2002 | Nakamura et al. |
| 2002/0120723 A1 | 8/2002 | Forth et al. |
| 2002/0123365 A1 | 9/2002 | Thorson |
| 2002/0142791 A1 | 10/2002 | Chen et al. |
| 2002/0159545 A1 | 10/2002 | Ramesh et al. |
| 2002/0169986 A1 | 11/2002 | Lortz |
| 2002/0196187 A1 | 12/2002 | Holt |
| 2003/0028621 A1 | 2/2003 | Furlong et al. |
| 2003/0101254 A1 | 5/2003 | Sato |
| 2003/0109271 A1 | 6/2003 | Lewis et al. |
| 2003/0125044 A1 | 7/2003 | Deloach |
| 2003/0125048 A1 | 7/2003 | Lockhart et al. |
| 2003/0133558 A1 | 7/2003 | Kung et al. |
| 2003/0139180 A1 | 7/2003 | McIntosh et al. |
| 2003/0142637 A1 | 7/2003 | Khawer et al. |
| 2003/0144793 A1 | 7/2003 | Melaku et al. |
| 2003/0153302 A1 | 8/2003 | Lewis et al. |
| 2003/0185375 A1 | 10/2003 | Albal |
| 2004/0003285 A1 | 1/2004 | Whelan |
| 2004/0111382 A1 | 6/2004 | Haji-Ioannou |
| 2004/0125781 A1 | 7/2004 | Walter et al. |
| 2004/0139201 A1 | 7/2004 | Chaudhary et al. |
| 2004/0165546 A1 | 8/2004 | Roskind |
| 2004/0203846 A1 | 10/2004 | Caronni et al. |
| 2004/0235455 A1 | 11/2004 | Jiang |
| 2004/0236702 A1 | 11/2004 | Fink et al. |
| 2004/0258003 A1 | 12/2004 | Kokot et al. |
| 2004/0264428 A1 | 12/2004 | Choi et al. |

(56) References Cited

U.S. PATENT DOCUMENTS

| | | |
|---|---|---|
| 2005/0003797 A1 | 1/2005 | Baldwin |
| 2005/0009499 A1 | 1/2005 | Koster |
| 2005/0020216 A1 | 1/2005 | Bune |
| 2005/0024201 A1 | 2/2005 | Culpepper et al. |
| 2005/0026650 A1 | 2/2005 | Russell |
| 2005/0030929 A1 | 2/2005 | Swier |
| 2005/0075114 A1 | 4/2005 | Dennison et al. |
| 2005/0108257 A1 | 5/2005 | Ishii et al. |
| 2005/0108529 A1 | 5/2005 | Juneau |
| 2005/0135375 A1 | 6/2005 | Hurtta et al. |
| 2005/0143057 A1 | 6/2005 | Shiraga et al. |
| 2005/0144279 A1 | 6/2005 | Wexelblat |
| 2005/0160276 A1 | 7/2005 | Braun et al. |
| 2005/0172148 A1 | 8/2005 | Ying |
| 2005/0177645 A1 | 8/2005 | Dowling et al. |
| 2005/0223389 A1 | 10/2005 | Klein et al. |
| 2005/0239448 A1 | 10/2005 | Bayne |
| 2005/0239498 A1 | 10/2005 | Dorenbosch et al. |
| 2005/0250527 A1 | 11/2005 | Jugl |
| 2005/0254451 A1 | 11/2005 | Grosbach |
| 2005/0255893 A1 | 11/2005 | Jin et al. |
| 2005/0259654 A1 | 11/2005 | Faulk, Jr. |
| 2005/0269402 A1 | 12/2005 | Spitzer et al. |
| 2005/0283518 A1 | 12/2005 | Sargent |
| 2006/0031387 A1 | 2/2006 | Hamzeh et al. |
| 2006/0031493 A1 | 2/2006 | Cugi |
| 2006/0046647 A1 | 3/2006 | Parikh et al. |
| 2006/0074814 A1 | 4/2006 | Lovell et al. |
| 2006/0075098 A1 | 4/2006 | Becker et al. |
| 2006/0101019 A1 | 5/2006 | Nelson et al. |
| 2006/0107327 A1 | 5/2006 | Sprigg et al. |
| 2006/0182074 A1 | 8/2006 | Kubler et al. |
| 2006/0223498 A1 | 10/2006 | Gallagher et al. |
| 2006/0224750 A1 | 10/2006 | Davies et al. |
| 2006/0244589 A1 | 11/2006 | Schranz |
| 2006/0281457 A1 | 12/2006 | Huotari et al. |
| 2007/0002844 A1 | 1/2007 | Ali |
| 2007/0008894 A1 | 1/2007 | Lynch et al. |
| 2007/0025245 A1 | 2/2007 | Porras et al. |
| 2007/0032225 A1 | 2/2007 | Konicek et al. |
| 2007/0032269 A1 | 2/2007 | Shostak |
| 2007/0041350 A1 | 2/2007 | Famolari |
| 2007/0066318 A1 | 3/2007 | Danzeisen et al. |
| 2007/0074272 A1 | 3/2007 | Watanabe |
| 2007/0094601 A1 | 4/2007 | Greenberg et al. |
| 2007/0094716 A1 | 4/2007 | Farino et al. |
| 2007/0097093 A1 | 5/2007 | Oshita et al. |
| 2007/0097938 A1 | 5/2007 | Nylander et al. |
| 2007/0097939 A1 | 5/2007 | Nylander et al. |
| 2007/0097983 A1 | 5/2007 | Nylander et al. |
| 2007/0099561 A1 | 5/2007 | Voss |
| 2007/0104166 A1 | 5/2007 | Rahman et al. |
| 2007/0111706 A1 | 5/2007 | Kumar et al. |
| 2007/0123253 A1 | 5/2007 | Simongini et al. |
| 2007/0124802 A1 | 5/2007 | Anton et al. |
| 2007/0129045 A1 | 6/2007 | Aerrabotu |
| 2007/0133563 A1 | 6/2007 | Hundscheidt et al. |
| 2007/0150732 A1 | 6/2007 | Suzuki et al. |
| 2007/0155421 A1 | 7/2007 | Alberth et al. |
| 2007/0167175 A1 | 7/2007 | Wong |
| 2007/0183427 A1 | 8/2007 | Nylander et al. |
| 2007/0184815 A1 | 8/2007 | Aebi |
| 2007/0199076 A1 | 8/2007 | Rensin et al. |
| 2007/0220252 A1 | 9/2007 | Sinko et al. |
| 2007/0232332 A1 | 10/2007 | Holur et al. |
| 2007/0258418 A1 | 11/2007 | Wurtenberger et al. |
| 2007/0263608 A1 | 11/2007 | Han et al. |
| 2007/0270152 A1 | 11/2007 | Nylander et al. |
| 2007/0275739 A1 | 11/2007 | Blackburn |
| 2007/0287501 A1 | 12/2007 | Hoshina |
| 2007/0297373 A1 | 12/2007 | Saifullah et al. |
| 2008/0043972 A1 | 2/2008 | Ruetschi et al. |
| 2008/0049702 A1 | 2/2008 | Meylan et al. |
| 2008/0065752 A1 | 3/2008 | Ch'ng et al. |
| 2008/0070547 A1 | 3/2008 | Schreyer |
| 2008/0072292 A1 | 3/2008 | Narjala |
| 2008/0076386 A1 | 3/2008 | Khetawat |
| 2008/0076392 A1 | 3/2008 | Khetawat et al. |
| 2008/0076393 A1 | 3/2008 | Khetawat et al. |
| 2008/0076398 A1 | 3/2008 | Mate et al. |
| 2008/0076412 A1 | 3/2008 | Khetawat et al. |
| 2008/0076419 A1 | 3/2008 | Khetawat et al. |
| 2008/0076420 A1 | 3/2008 | Khetawat et al. |
| 2008/0076425 A1 | 3/2008 | Khetawat et al. |
| 2008/0081636 A1 | 4/2008 | Nylander et al. |
| 2008/0082538 A1 | 4/2008 | Meijer et al. |
| 2008/0084291 A1 | 4/2008 | Campion et al. |
| 2008/0119160 A1 | 5/2008 | Andriantsiferana et al. |
| 2008/0126531 A1 | 5/2008 | Setia et al. |
| 2008/0132239 A1 | 6/2008 | Khetawat et al. |
| 2008/0133742 A1 | 6/2008 | Southiere et al. |
| 2008/0141348 A1 | 6/2008 | Hovnanian et al. |
| 2008/0151807 A1 | 6/2008 | Meier et al. |
| 2008/0162489 A1 | 7/2008 | Reponen et al. |
| 2008/0168099 A1 | 7/2008 | Skaf |
| 2008/0181184 A1 | 7/2008 | Kezys |
| 2008/0201076 A1 | 8/2008 | Huang et al. |
| 2008/0207170 A1 | 8/2008 | Khetawat et al. |
| 2008/0242280 A1 | 10/2008 | Shapiro et al. |
| 2008/0244148 A1 | 10/2008 | Nix et al. |
| 2008/0254792 A1 | 10/2008 | Ch'ng |
| 2008/0261602 A1 | 10/2008 | Livneh |
| 2008/0274753 A1 | 11/2008 | Attar et al. |
| 2008/0281687 A1 | 11/2008 | Hurwitz et al. |
| 2008/0282327 A1 | 11/2008 | Winget et al. |
| 2008/0293382 A1 | 11/2008 | Lubenski et al. |
| 2008/0293433 A1 | 11/2008 | Wallis |
| 2008/0299984 A1 | 12/2008 | Shimomura |
| 2008/0299992 A1 | 12/2008 | Eitan et al. |
| 2008/0305792 A1 | 12/2008 | Khetawat et al. |
| 2008/0305801 A1 | 12/2008 | Burgess et al. |
| 2008/0305834 A1 | 12/2008 | Janiszewski et al. |
| 2008/0318551 A1 | 12/2008 | Palamara et al. |
| 2009/0012898 A1 | 1/2009 | Sharma et al. |
| 2009/0031006 A1 | 1/2009 | Johnson et al. |
| 2009/0037973 A1 | 2/2009 | Gustave et al. |
| 2009/0042593 A1 | 2/2009 | Yavuz et al. |
| 2009/0046632 A1 | 2/2009 | Nanda et al. |
| 2009/0046665 A1 | 2/2009 | Robson et al. |
| 2009/0047945 A1 | 2/2009 | Zhang |
| 2009/0059822 A1 | 3/2009 | Morrill et al. |
| 2009/0061821 A1 | 3/2009 | Chen et al. |
| 2009/0061873 A1 | 3/2009 | Bao et al. |
| 2009/0077620 A1 | 3/2009 | Ravi et al. |
| 2009/0082010 A1 | 3/2009 | Lee |
| 2009/0082020 A1 | 3/2009 | Ch'ng et al. |
| 2009/0092080 A1 | 4/2009 | Balasubramanian et al. |
| 2009/0092081 A1 | 4/2009 | Balasubramanian et al. |
| 2009/0092096 A1 | 4/2009 | Czaja |
| 2009/0092097 A1 | 4/2009 | Nylander et al. |
| 2009/0093232 A1 | 4/2009 | Gupta et al. |
| 2009/0094351 A1 | 4/2009 | Gupta et al. |
| 2009/0094680 A1 | 4/2009 | Gupta et al. |
| 2009/0097436 A1 | 4/2009 | Vasudevan et al. |
| 2009/0098871 A1 | 4/2009 | Gogic |
| 2009/0109979 A1 | 4/2009 | Tong |
| 2009/0111499 A1 | 4/2009 | Bosch |
| 2009/0119750 A1 | 5/2009 | Sembugamoorthy et al. |
| 2009/0122773 A1 | 5/2009 | Gogic |
| 2009/0124262 A1 | 5/2009 | Vela et al. |
| 2009/0129336 A1 | 5/2009 | Osborn et al. |
| 2009/0129350 A1 | 5/2009 | Khandekar et al. |
| 2009/0131050 A1 | 5/2009 | Osborn |
| 2009/0131098 A1 | 5/2009 | Khandekar et al. |
| 2009/0135749 A1 | 5/2009 | Yang |
| 2009/0135794 A1 | 5/2009 | Su et al. |
| 2009/0156213 A1 | 6/2009 | Spinelli et al. |
| 2009/0161682 A1 | 6/2009 | Johnson et al. |
| 2009/0163216 A1 | 6/2009 | Hoang et al. |
| 2009/0163224 A1 | 6/2009 | Dean |
| 2009/0164547 A1* | 6/2009 | Ch'ng .................. H04W 48/08 709/201 |
| 2009/0170440 A1 | 7/2009 | Eyuboglu et al. |
| 2009/0170528 A1 | 7/2009 | Bull et al. |

(56) References Cited

U.S. PATENT DOCUMENTS

| | | | |
|---|---|---|---|
| 2009/0180428 A1 | 7/2009 | Viswanath | |
| 2009/0191844 A1 | 7/2009 | Morgan et al. | |
| 2009/0191845 A1* | 7/2009 | Morgan | H04W 48/02 455/411 |
| 2009/0210324 A1 | 8/2009 | Bhogal | |
| 2009/0213825 A1 | 8/2009 | Gupta et al. | |
| 2009/0215429 A1 | 8/2009 | Caldwell et al. | |
| 2009/0215452 A1 | 8/2009 | Balasubramanian et al. | |
| 2009/0221303 A1* | 9/2009 | Soliman | H04W 52/0274 455/458 |
| 2009/0233574 A1 | 9/2009 | Shinozaki | |
| 2009/0245176 A1 | 10/2009 | Balasubramanian et al. | |
| 2009/0247157 A1 | 10/2009 | Yoon et al. | |
| 2009/0253421 A1 | 10/2009 | Camp et al. | |
| 2009/0253432 A1 | 10/2009 | Willey et al. | |
| 2009/0257434 A1 | 10/2009 | Song et al. | |
| 2009/0279701 A1 | 11/2009 | Moisand et al. | |
| 2009/0288152 A1 | 11/2009 | Huber | |
| 2009/0291667 A1 | 11/2009 | Vakil et al. | |
| 2009/0299788 A1 | 12/2009 | Huber et al. | |
| 2009/0325634 A1 | 12/2009 | Bienas et al. | |
| 2010/0022266 A1 | 1/2010 | Villier | |
| 2010/0027469 A1 | 2/2010 | Gurajala et al. | |
| 2010/0040026 A1 | 2/2010 | Melkesetian | |
| 2010/0048165 A1 | 2/2010 | Caldwell et al. | |
| 2010/0056104 A1 | 3/2010 | Butler | |
| 2010/0075658 A1 | 3/2010 | Hou | |
| 2010/0113067 A1 | 5/2010 | Fullam et al. | |
| 2010/0157941 A1 | 6/2010 | Raghothaman | |
| 2010/0167771 A1 | 7/2010 | Raghothaman et al. | |
| 2010/0167777 A1 | 7/2010 | Raghothaman et al. | |
| 2010/0260068 A1 | 10/2010 | Bhatt et al. | |
| 2010/0271962 A1 | 10/2010 | Han | |
| 2011/0055928 A1 | 3/2011 | Brindza | |
| 2011/0086614 A1 | 4/2011 | Brisebois et al. | |
| 2011/0134837 A1 | 6/2011 | Wang et al. | |
| 2011/0177794 A1 | 7/2011 | Nylander et al. | |
| 2011/0200022 A1 | 8/2011 | Annamalai | |
| 2011/0280154 A1 | 11/2011 | Silverstrim et al. | |
| 2012/0135712 A1 | 5/2012 | Bari | |
| 2012/0258711 A1 | 10/2012 | Bao et al. | |
| 2013/0165079 A1 | 6/2013 | Gogic | |

FOREIGN PATENT DOCUMENTS

| | | |
|---|---|---|
| CN | 101175333 A | 5/2008 |
| EP | 2286569 | 2/2011 |
| GB | 2425291 A | 10/2006 |
| GB | 2425921 A | 11/2006 |
| JP | 20010264096 | 9/2001 |
| JP | 2003022303 | 1/2003 |
| JP | 2003088521 | 10/2003 |
| JP | 2004112324 | 4/2004 |
| JP | 2005073147 | 3/2005 |
| JP | 2005215849 | 8/2005 |
| JP | 20060674143 | 3/2006 |
| JP | 2008048055 | 2/2008 |
| WO | 02-14987 A2 | 2/2002 |
| WO | 2005076964 A2 | 8/2005 |
| WO | 2007015067 A2 | 2/2007 |
| WO | 2007040449 A1 | 4/2007 |
| WO | 2008047039 A1 | 4/2008 |

OTHER PUBLICATIONS

International Search Report and Written Opinion mailed Feb. 23, 2010, for PCT Application No. PCT/US2009/043846, 13 pages.
Office Action dated Dec. 31, 2009 for U.S. Appl. No. 11/457,129, 16 pages.
Office Action dated Apr. 17, 2009 for U.S. Appl. No. 11/276,269, 15 pages.
Office Action dated Nov. 4, 2008 for U.S. Appl. No. 11/276,269, 15 pages.
Office Action dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
Office Action dated Mar. 29, 2011 for U.S. Appl. No. 12/276,002, 37 pages.
Office Action dated Apr. 13, 2011 for U.S. Appl. No. 12/276,058, 40 pages.
Office Action dated Apr. 19, 2011 for U.S. Appl. No. 12/276,238, 22 pages.
Office Action dated May 5, 2011 for U.S. Appl. No. 12/275,015, 32 pages.
Office Action dated Jun. 14, 2011 for U.S. Appl. No. 12/275,878, 35 pages.
Office Action dated Jun. 22, 2011 for U.S. Appl. No. 12/484,072, 38 pages.
Office Action dated Jul. 7, 2011 for U.S. Appl. No. 12/276,257, 24 pages.
Office Action dated Jun. 28, 2011 for U.S. Appl. No. 12/275,925, 18 pages.
Office Action dated Jun. 8, 2011 for U.S. Appl. No. 12/484,026, 30 pages.
Office Action dated Aug. 18, 2011 for U.S. Appl. No. 12/275,416, 39 pages.
Office Action dated Sep. 14, 2011 for U.S. Appl. No. 12/276,002, 35 pages.
Office Action dated Oct. 5, 2011 for U.S. Appl. No. 12/276,058, 37 pages.
Office Action dated Oct. 6, 2011 for U.S. Appl. No. 12/465,483, 50 pages.
Office Action dated Oct. 4, 2011 for U.S. Appl. No. 12/484,135, 44 pages.
Office Action dated Jul. 21, 2011 for U.S. Appl. No. 12/175,293, 30 pages.
Office Action dated Oct. 24, 2011 for U.S. Appl. No. 12/275,925, 14 pages.
Office Action dated Nov. 30, 2011 for U.S. Appl. No. 12/275,878, 38 pages.
Office Action dated Dec. 1, 2011 for U.S. Appl. No. 12/275,996, 44 pages.
Office Action dated Oct. 25, 2011 for U.S. Appl. No. 12/465,580, 39 pages.
Office Action dated Nov. 8, 2011 for U.S. Appl. No. 12/465,468, 50 pages.
Office Action dated Jan. 5, 2012 for U.S. Appl. No. 12/465,585, 43 pages.
Office Action dated Dec. 28, 2011 for U.S. Appl. No. 12/175,293, 38 pages.
Office Action dated Nov. 21, 2011 for U.S. Appl. No. 12/484,026, 37 pages.
Office Action dated Dec. 14, 2011 for U.S. Appl. No. 12/484,072, 44 pages.
Office Action dated Nov. 1, 2011 for U.S. Appl. No. 12/816,087, 33 pages.
Office Action dated Mar. 5, 2012 for U.S. Appl. No. 12/465,598, 55 pages.
Office Action dated May 8, 2012 for U.S. Appl. No. 11/457,129, 38 pages.
Office Action dated Mar. 19, 2012 for U.S. Appl. No. 12/276,120, 68 pages.
Office Action dated Mar. 30, 2012 for U.S. Appl. No. 12/484,026, 30 pages.
Notice of Allowance dated Apr. 3, 2012 for U.S. Appl. No. 12/275,996, 38 pages.
Office Action dated Apr. 10, 2012 for U.S. Appl. No. 12/275,416, 32 pages.
Office Action dated Apr. 10, 2012 for U.S. Appl. No. 12/484,135, 45 pages.
Notice of Allowance dated Apr. 25, 2012 for U.S. Appl. No. 12/465,468, 35 pages.

(56) References Cited

OTHER PUBLICATIONS

Office Action dated Jul. 16, 2012 for U.S. Appl. No. 12/275,878, 37 pages.
Office Action dated Jul. 10, 2012 for U.S. Appl. No. 12/465,585, 32 pages.
Office Action dated Apr. 13, 2012 for U.S. Appl. No. 13/316,106, 35 pages.
Office Action dated Sep. 5, 2012 for U.S. Appl. No. 12/276,120, 49 pages.
Office Action dated Aug. 16, 2012 for U.S. Appl. No. 12/465,598, 31 pages.
Office Action dated Sep. 6, 2012 for U.S. Appl. No. 12/579,957, 51 pages.
Office Action dated Sep. 10, 2012 for U.S. Appl. No. 12/276,002, 54 pages.
Office Action dated Oct. 2, 2012 for U.S. Appl. No. 12/484,026, 29 pages.
Office Action dated Oct. 11, 2012 for U.S. Appl. No. 13/487,794, 45 pages.
Office Action dated Oct. 9, 2012 for U.S. Appl. No. 13/298,924, 51 pages.
Office Action dated Oct. 30, 2015 for U.S. Appl. No. 13/949,983, 19 pages.
Final Office Action dated Jan. 21, 2016 for U.S. Appl. No. 12/276,120, 108 pages.
Final Office Action dated Jan. 21, 2016 for U.S. Appl. No. 12/465,585, 28 pages.
Office Action dated Nov. 1, 2012 for U.S. Appl. No. 12/276,058, 59 pages.
Office Action dated Nov. 5, 2012 for U.S. Appl. No. 12/484,072, 52 pages.
Office Action dated Nov. 20, 2012 for U.S. Appl. No. 12/275,878, 28 pages.
Japanese Office Action mailed Sep. 13, 2012 for Japanese Patent Application No. 2011-509669, 10 pages.
Canadian Office Action mailed Oct. 30, 2012 for Canadian Patent Application No. 2,722,324, 3 pages.
Japanese Office Action mailed Sep. 13, 2012 for Japanese Patent Application No. 2011-509675, 4 pages.
Office Action dated Dec. 3, 2012 for U.S. Appl. No. 12/275,416, 33 pages.
Office Action dated Jan. 17, 2013 for U.S. Appl. No. 13/554,710, 42 pages.
Final Office Action dated Feb. 15, 2013 for U.S. Appl. No. 12/579,957.
Office Action dated Feb. 26, 2013 for U.S. Appl. No. 12/276,120, 59 pages.
Chinese Office Action for Chinese Application No. 200980117263.8 dated Feb. 16, 2013, 7 pages.
Chinese Office Action for Chinese Application No. 200980117188.5 dated Jan. 31, 2013, 11 pages.
Final Office Action dated Mar. 14, 2013 for U.S. Appl. No. 12/484,072, 34 pages.
Office Action dated Apr. 23, 2013 for U.S. Appl. No. 12/175,293, 41 pages.
Canadian Office Action mailed Mar. 26, 2013 for Canadian Patent Application No. 2,722,324,4 pages.
Office Action dated Jul. 15, 2013 for U.S. Appl. No. 13/554,710, 37 pages.
Office Action dated Aug. 13, 2013 for U.S. Appl. No. 121276,120, 66 pages.
Office Action dated Aug. 12, 2013 for U.S. Appl. No. 12/275,416, 36 pages.
Office Action dated Sep. 9, 2013 for U.S. Appl. No. 12/465,585, 45 pages.
Office Action dated Oct. 2, 2013 for U.S. Appl. No. 12/275,878, 38 pages.
Office Action dated Oct. 3, 2013 for U.S. Appl. No. 13/892,923, 62 pages.
Office Action dated Oct. 22, 2013 for U.S. Appl. No. 13/898,910, 50 pages.
Office Action dated Oct. 3, 2013 for U.S. Appl. No. 13/934,644, 17 pages.
Chinese Office Action dated Oct. 24, 2013 for Chinese Patent Application No. 200980117263.8, 13 pages.
Chinese Office Action dated Oct. 21, 2013 for Chinese Patent Application No. 200980117188.5, 11 pages.
Japanese Office Action dated Oct. 3, 2013 for Japanese Patent Application No. 2011-509669, 15 pages.
Office Action dated Dec. 12, 2013 for U.S. Appl. No. 12/276,120, 78 pages.
Notice of Allowance dated Feb. 13, 2014 for U.S. Appl. No. 12/275,878, 34 pages.
Hasan, Mohammad Masud; Huang, Xiadong; Jue, Jason P.; "Survivable Wireless Access Network Design with Dual-homing Capabilities"; IEEE Global Telecommunications Conference, Nov. 27-Dec. 1, 2006, 5 pgs.
Japanese Office Action dated Jan. 16, 2014 for Japanese Patent Application No. 2013-026198, 8 pages.
Office Action dated Mar. 26, 2014 for U.S. Appl. No. 12/465,585, 44 pages.
Office Action dated Mar. 24, 2014 for U.S. Appl. No. 13/934,644, 50 pages.
Notice of Allowance dated Apr. 4, 2014 for U.S. Appl. No. 14/090,802, 63 pages.
Office Action dated Mar. 24, 2014 for U.S. Appl. No. 13/671,191, 63 pages.
Office Action dated Jun. 9, 2014 for U.S. Appl. No. 12/276,120, 92 Pages.
Office Action dated Jun. 11, 2014 for U.S. Appl. No. 13/675,150, 68 Pages.
Chinese Office Action dated Jun. 19, 2014 for Chinese Patent Application No. 200980117188.5, 5 Pages.
Canadian Office Action dated May 13, 2014 for Canadian Patent Application 2,722,367, 5 Pages.
Office Action dated Jun. 10, 2014 for U.S. Appl. No. 14/253,553, 16 pages.
Office Action dated Sep. 9, 2014 for U.S. Appl. No. 12/276,120, 93 pages.
Office Action dated Nov. 6, 2014 for U.S. Appl. No. 12/465,585, 43 pages.
Chinese Office Action dated Dec. 22, 2014 for Chinese Patent Application No. 200980117188.5, 4 Pages.
Office Action dated Dec. 23, 2014 for U.S. Appl. No. 13/917,153, 90 pages.
Office Action dated Feb. 4, 2015 for U.S. Appl. No. 13/949,983, 90 pages.
European Office Action dated Feb. 2, 2015 for European Patent Application No. 09747521.4, 4 pages.
Office Action dated Feb. 19, 2015 for U.S. Appl. No. 12/276,120, 90 pages.
Office Action dated Mar. 13, 2015 for U.S. Appl. No. 12/465,585, 39 Pages.
Office Action dated Apr. 17, 2015 for U.S. Appl. No. 14/286,414, 55 Pages.
Office Action dated Mar. 30, 2015 for U.S. Appl. No. 14/219,543, 81 Pages.
Office Action dated Mar. 26, 2015 for U.S. Appl. No. 14/472,012, 62 Pages.
Office Action dated May 18, 2015 for U.S. Appl. No. 14/567,839, 59 Pages.
Canadian Office Action dated Apr. 7, 2015 for Canadian Patent Application No. 2,722,367, 6 Pages.
Office Action dated May 5, 2015 for U.S. Appl. No. 14/660,549, 25 pages.
Office Action dated Jun. 29, 2015 for U.S. Appl. No. 13/949,983, 39 pages.
Office Action dated Jul. 13, 2015 for U.S. Appl. No. 14/520,274, 69 pages.
Office Action dated Jul. 22, 2015 for U.S. Appl. No. 12/276,120, 120 pages.

(56) References Cited

OTHER PUBLICATIONS

Chinese Office Action dated Jun. 30, 2015 for Chinese Patent Application No. 200980117188.5, 7 pages.
Office Action dated Sep. 24, 2015 for U.S. Appl. No. 14/472,012, 40pgs.
Office Action dated Aug. 19, 2015 for U.S. Appl. No. 12/465,585, 42 pages.
Office Action dated Aug. 20, 2015 for U.S. Appl. No. 14/219,543, 43 pages.
Office Action dated Sep. 11, 2015 for U.S. Appl. No. 14/286,414, 28 pages.
Office Action dated Feb. 8, 2016 for U.S. Appl. No. 14/219,543, 40 pages.
Office Action dated Mar. 17, 2016 for U.S. Appl. No. 12/484,072, 97 pages.
Office Action dated Apr. 6, 2016 for U.S. Appl. No. 14/455,614, 97 pages.
Office Action dated Feb. 3, 2016 for U.S. Appl. No. 14/472,012, 42 pages.
Notice of Allowance mailed Feb. 3, 2016 for U.S. Appl. No. 14/739,859, 73 pages.
Notice of Allowance mailed Jul. 22, 2016 for U.S. Appl. No. 14/472,012, 45 pages.
Office Action dated Jun. 29, 2016 for U.S. Appl. No. 12/276,120, 106 pages.
European Office Action dated May 9, 2016 for European Patent Application No. 09752238.7, 2 pages.
Office Action dated Aug. 18, 2016 for U.S. Appl. No. 15/048,971, 67 pages.
Office Action dated Aug. 22, 2016 for U.S. Appl. No. 12/465,585, 8 pages.
Office Action dated Oct. 3, 2016 for U.S. Appl. No. 12/484,072, 40 pages.
Office Action dated Nov. 3, 2016 for U.S. Appl. No. 15/235,099, 33 pages.

\* cited by examiner

INTERFACE FOR ACCESS MANAGEMENT OF FEMTO CELL COVERAGE

CROSS-REFERENCE

The subject application is a continuation of, and claims priority to each of, U.S. patent application Ser. No. 13/917,153, entitled "INTERFACE FOR ACCESS MANAGEMENT OF FEMTO CELL COVERAGE," and filed on Jun. 13, 2013, which is a continuation of U.S. Pat. No. 8,490,156, entitled "INTERFACE FOR ACCESS MANAGEMENT OF FEMTO CELL COVERAGE," and filed on Nov. 21, 2008, which claims the benefit of U.S. Provisional Application No. 61/052,813, entitled "MANAGEMENT OF ACCESS TO FEMTO CELL COVERAGE," and filed May 13, 2008. The entireties of each of the above noted applications are incorporated herein by reference.

TECHNICAL FIELD

The present disclosure relates generally to wireless communications and, more particularly, to management of access to femto cell coverage by a subscriber and subscriber stations.

BACKGROUND

Femto cells—building-based wireless access points interfaced with a wired broadband network—are generally deployed to improve indoor wireless coverage provided by a wireless network operator. Femto cells typically operate in licensed portions of the electromagnetic spectrum, and generally offer plug-and-play installation; e.g., automatic configuration of femto access point. Improved indoor coverage includes stronger signal and improved reception (e.g., voice or sound), ease of session or call initiation and session or call retention as well. Coverage of a femto cell, or femto AP, is intended to be confined within the bounds of an indoor compound, in order to mitigate interference among mobile stations covered by a macro cell and terminals covered by the femto AP. Additionally, confined coverage can reduce cross-talk among terminals serviced by disparate, neighboring femto cells as well.

Coverage improvements via femto cells can also mitigate customer attrition as long as a favorable subscriber perception regarding voice coverage and other data services with substantive delay sensitivity is attained. A positive customer experience can depend on adequate access management to femto cell service.

DETAILED DESCRIPTION

Figure 1:
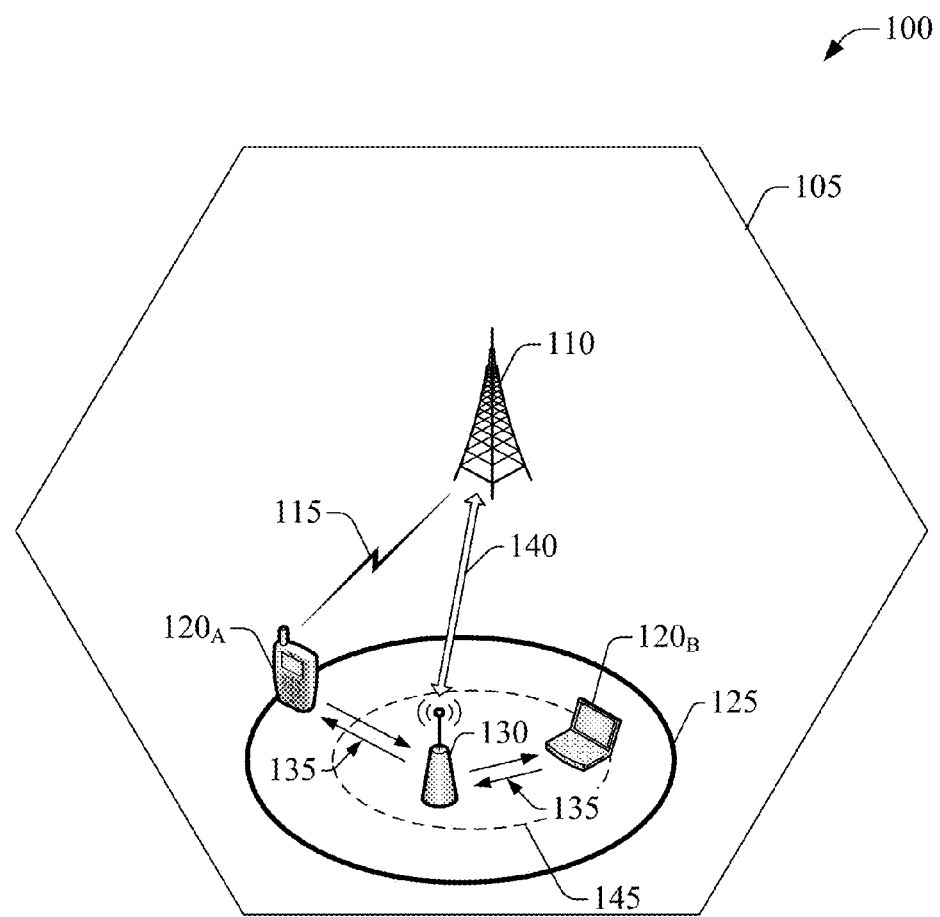
FIG. 1 a schematic deployment of a macro cell and a femto cell for wireless coverage in accordance with aspects described herein.

The subject application is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "system," "platform," and the like are intended to refer to a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," "subscriber station," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "user," "subscriber," "customer," "consumer," "prosumer," "agent," and the like are employed interchangeably throughout the subject specification, unless context warrants particular distinction(s) among the terms. As utilized herein, the term "prosumer" indicate the following contractions: professional-consumer and producer-consumer.

The following abbreviations are relevant to the subject specification.
3G Third Generation
3GPP Third Generation Partnership Project
AGPS Assisted GPS
AP Access Point
ADSL Asymmetric Digital Subscriber Line
AWS Advanced Wireless Services
BRAS Broadband Remote Access Server
BTA Basic Trading Area
CN Core Network
CS Circuit-Switched
CSCF Call Session Control Function
CPE Customer Premise Equipment
CPN Customer Premise Network
DHCP Dynamic Host Configuration Protocol
DSL Digital Subscriber Line
DSLAM Digital Subscriber Line Access Multiplexer
E911 Enhanced 911
FCC Federal Communications Commission
FL Forward Link
GGSN Gateway GPRS Service Node
GPRS General Packet Radio Service
GPS Global Positioning System
GW Gateway
HAP Home Access Point
HSS Home Subscriber Server
ISDN Integrated Services Digital Network
UE User Equipment
UTRAN Universal Terrestrial Radio Access Network
IMS IP Multimedia Subsystem
IP Internet Protocol
ISP Internet Service Provider
MSA Metropolitan Statistical Areas
MSISDN Mobile Subscriber ISDN Number
MTA Major Trading Areas
NAT Network Address Translation
NTP Network Time Protocol
O&M Operation and Maintenance
PC Personal Computer
PCS Personal Communications Service
PS Packet-Switched
PSTN Public Switched Telephone Network
RAN Radio Access Network
RBS Radio Base Station
RL Reverse Link
RNC Radio Network Controller
RSA Rural Service Area
SGSN Serving GPRS Support Node
SIP Session Initiation Protocol
USSD Unstructured Supplementary Service Data
VPN Virtual Private Network
WAP Wireless Application Protocol
XDSL Asynchronous-DSL or Synchronous-DSL System(s) and method(s) to manage access to femto cell service through access control list(s), or "white list(s)" are disclosed herein. Such white list(s) can be configured via a networked interface which facilitates access management to a femto cell. White list(s) includes a set of subscriber station(s) identifier numbers, codes or tokens, and can also include additional fields for femto cell access management based on desired complexity. Various example aspects such as white list(s) management, maintenance and dissemination; pre-configuration; and inclusion of wireless device(s) or subscriber(s) are discussed herein.

An aspect relates to a system that facilitates management of access to femto cell coverage. The system comprises an interface component and an access management component. The interface component configures an access control list for femto cell coverage. The access management component grants access to femto cell coverage based on the contents of the access control list. The interface component further comprises a user profile component that provides an interface to the user to grant a requesting UE access rights to the femto cell resources based at least on a profile associated with the user. For example, if the user is a primary administrator, a detailed interface is provided whereas for a secondary user, an abbreviated interface can be presented. The detailed interface can be employed to set a specific access level for a requesting UE whereas the abbreviated interface can grant temporary access (or a specified default level of access rights associated therewith) to a requesting UE. A timer is associated with the temporary access granted to the UE such that upon expiration of a time period associated with the timer, a request to extend access rights of the UE is forwarded to the user. The interface component further comprises an intelligent component that presents an appropriate interface based on one or more of the user profile or device parameters. The access management component can provide access to one or more requesting UEs based at least on a type of interface presented to the user by the interface. The interface component can also comprise a display component that displays IDs and/or access details of one or more UEs associated with the access control list in addition to various options to administer the access control list such as options to add, delete and/or edit numbers in the list.

Another aspect relates to a method of providing access to femto resources. The method comprises the steps of configuring an access control list for femto cell service and granting access to femto cell service according to the configured access control list. The access control list can be configured using a web based GUI (graphical user interface) that facilitates one or more of addition, deletion or editing of IDs associated with UEs accessing the femto resources. The web-based GUI can provide a component to display access details of one of more UEs included in the access control list. In accordance with a further aspect, the web based GUI is provided to a primary administrator of the femto cell such that the administrator can provide a desired access level to a requesting UE. The access control list can also be edited via an abbreviated interface. The abbreviated interface can be provided to a secondary user via one or more alternate devices supplied for receiving femto cell management notifications. The secondary user can grant temporary access to the femto resources to a requesting UE wherein a timer is associated with the temporary access. An extension notification is provided to the user upon expiration of a time period associated with the temporary access such that the user has an option to either extend or revoke the access rights granted to the UE.

Another aspect relates to a system for providing access to femto cell resources. The system comprises means for configuring an access control list for femto cell service. Means for granting access to femto cell service, also included in the system, grants access to a requesting UE according to the configured access control list.

In yet another aspect, a computer-readable medium having instructions stored thereon that aid in femto cell resource management is disclosed. When executed by a processor, the instructions cause a computer to configure an access control list for femto cell service. The instructions also aid in granting access to femto cell service according to the configured access control list.

Referring to the drawings, FIG. 1A illustrates a schematic wireless environment (e.g., a network) 100 in which a femto cell can exploits various aspects described in the subject specification. In wireless environment 100, area 105 represents a coverage macro cell which is served by base station 110. Macro coverage is generally intended for outdoors locations for servicing mobile wireless devices, like UE 120$_A$, and such coverage is achieved via a wireless link 115. In an aspect, UE 120 can be a 3GPP Universal Mobile Telecommunication System (UMTS) mobile phone.

Within macro coverage cell 105, a femto cell 145, served by a femto access point 130, can be deployed. A femto cell typically covers an area 125 that is determined, at least in part, by transmission power allocated to femto AP 130, path loss, shadowing, and so forth. Coverage area typically is spanned by a coverage radius that ranges from 20 to 50 meters. Confined coverage area 145 is generally associated with an indoors area, or a building, which can span about 5000 sq. ft. Generally, femto AP 130 typically services a few wireless devices (e.g., subscriber station 120$_B$) within confined coverage area 145. In an aspect, femto AP 130 can integrate seamlessly with substantially any PS-based and CS-based network; for instance, femto AP 130 can integrate into an existing 3GPP Core via conventional interfaces like Iu-CS, Iu-PS, Gi, Gn. In another aspect, femto AP 130 can exploit high-speed downlink packet access in order to accomplish substantive bitrates. In yet another aspect, femto AP 130 has a LAC (location area code) and RAC (routing area code) that is different than the underlying macro network. These LAC and RAC are used to identify subscriber station location for a variety of reasons, most notably to direct incoming voice and data traffic to appropriate paging transmitters.

As a subscriber station, e.g., UE 120$_A$, leaves macro coverage (e.g., cell 105) and enters femto coverage (e.g., area 125), as illustrated in environment 100, UE 120$_A$ attempts to attach to the femto AP 130 through transmission and reception of attachment signaling, effected via a FL/RL 135; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that UE 120 can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 130) is therefore inclined to minimize unnecessary LAU/RAU signaling activity at substantially any opportunity to do so, and through substantially any available means. It is to be noted that substantially any mitigation of unnecessary attachment signaling/control is advantageous for femto cell operation. Conversely, if not successful, UE 120 is generally commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE 120 is allowed on femto AP 130 and incoming voice and data traffic are paged and routed to the subscriber through the femto AP 130. It is to be noted also that data traffic is typically routed through a backhaul broadband wired network backbone 140 (e.g., optical fiber backbone, twisted-pair line, T1/E1 phone line, DSL, or coaxial cable). To this end, femto AP 130 is connected to the broadband backhaul network backbone 140 via a broadband modem (not shown).

It is to be noted that as a femto AP 130 generally relies on a backhaul network backbone 140 for routing and paging, and for packet communication, substantially any quality of service handles heterogeneous packetized traffic. Namely, packet flows established for wireless devices (like terminals 120$_A$ and 120$_B$) served by femto AP 130, and for devices served through the backhaul network pipe 140. It is to be noted that to ensure a positive subscriber experience, or perception, it is important for femto AP 130 to maintain a high level of throughput for traffic (e.g., voice and data) utilized on a mobile device for one or more subscribers while in the presence of external, additional packetized, or broadband, traffic associated with applications (web browsing, data transfer (e.g., content upload), and the like) executed in devices within the femto coverage area (e.g., either area 125 or area 145).

Figure 2:
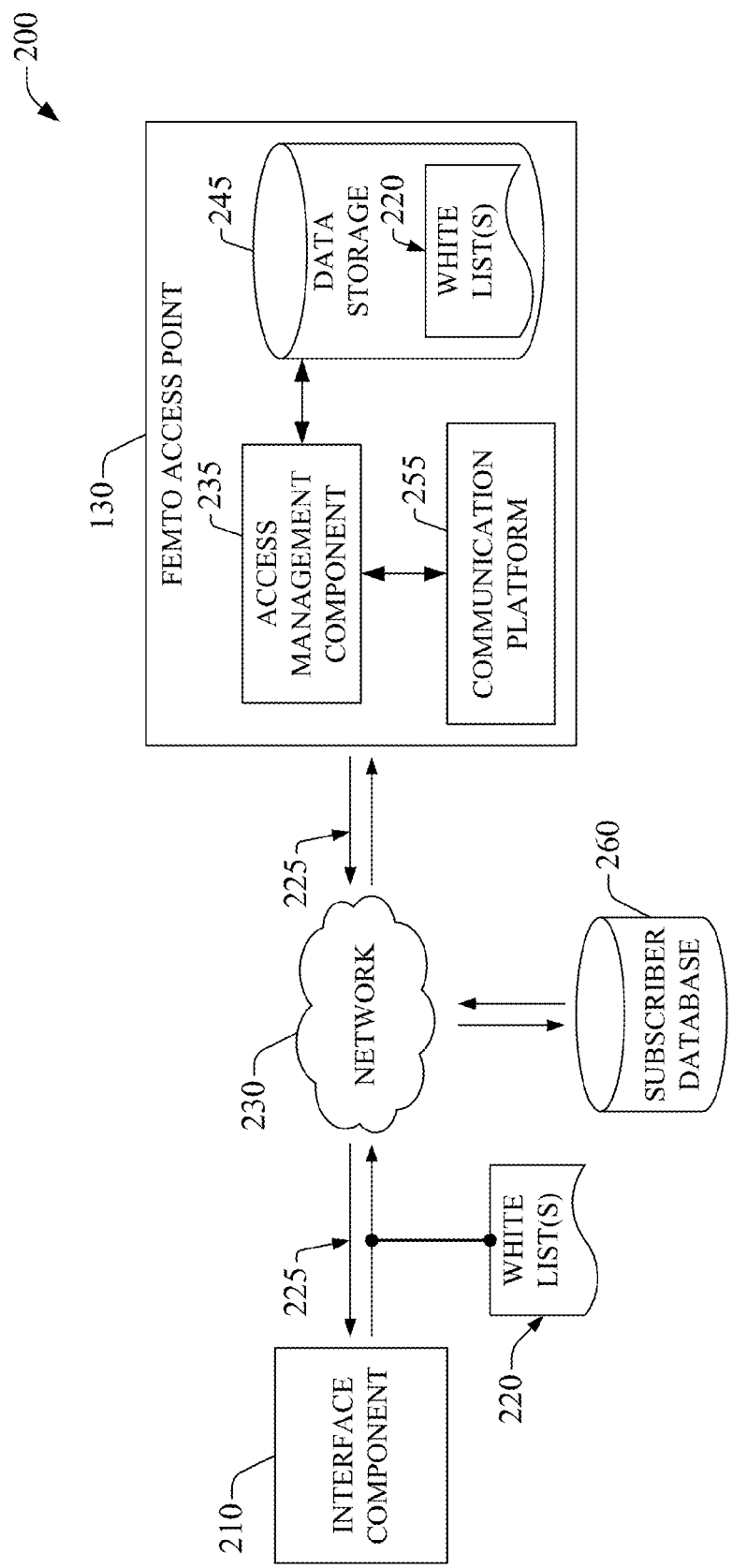
FIG. 2 is a block diagram of an example system that facilitates selection of subscribers to access coverage from a femto cell in accordance with aspects disclosed herein.

FIG. 2 is a block diagram of an example system 200 that facilitates selection of subscribers to access coverage from a femto cell; selection can enable or disable coverage for specific subscriber(s) or subscriber station(s). Means provided by example system 200 to authorize or revoke access to specific subscribers, or subscriber station(s), comprise what is herein termed as a "White List"—an instrument for management of access to femto cell coverage.

In example system 200, an interface component 210 facilitates configuration, or set up, of a list (e.g., white list 220) of wireless mobile station numbers approved for coverage through femto access point 130. It is to be noted that substantially any identification token(s), label(s), or code(s) that identify a subscriber station can be employed. Interface 210 is networked (e.g., via a WAN, LAN, or backhaul pipe) with femto AP 130 and convey white list 220 over network link(s) 225. In an aspect, interface component 210 can be a web-based, online graphic user interface (GUI); however, other networked interfaces that facilitates to enter, or configure, a white list are possible; for instance, voice or sound commanded interface(s), touch commanded interface(s), biometric commanded interfaces(s), and the like. A communication platform 255 facilitates reception of the white list(s) 220 and conveys white list(s) 220 to an access management component 235 that can exploit the white list(s) 220 to manage access to coverage provided by femto AP 130. White list(s) 220 can be stored in the data storage 245 in the femto AP 130; even though white list(s) 220 can be stored in disparate network components like network component administered by a service operator. In addition, interface component 210 can access a subscriber database through network 230, in order to extract identification numbers, codes, tokens, or labels for subscribers/subscriber stations that can be entered in a white list.

In an illustrative, not-limiting aspect of an embodiment, white list(s) 220 (or any set of numbers, codes or tokens thereon, that comprise a set of mobile phones approved for coverage by femto AP 130) can be portable through accounts or billing groups associated with a set of subscribers to a service operator that administers femto AP 130, or a macro network. As an illustration, white list(s) 220 can support up to N fields (N a positive integer; e.g., N=50) for unique mobile phone numbers (e.g., MSIDSNs), or any suitable identifying codes or tokens. The number N of fields can be determined, or configured, by a service operator based at least in part on technical aspects (like network resources, quality of service consideration, macro area of coverage (e.g., MSA/RSA), and so on) and commercial aspects (such as promotional considerations, mitigation of customer attrition, gains in market share, etc.) aspects of provision of coverage. As an example, N can be subscriber dependent or femto AP dependent.

In contrast to management of access authorization via femto access point 130, it should be appreciated that configuration of white list(s) 220 (registration authorization for femto coverage) through a network mechanisms (e.g., interface component 210) provides at least the following advantages. It is to be noted that the following advantages are illustrative and not limiting, as other advantages associated with white list(s) 220 are possible and are intended to lay within the scope of an embodiment(s) described in the subject specification. (1) Access through an networked interface (online or otherwise) reduces provisioning lead time and provides a means for customers to update and personalize femto AP autonomously (e.g., free of interaction with technical support entities) at substantially any time. (2) Security against devices attempting to hack into the femto AP when networked with it, and support of extensible sharing/networking of the authorization scheme. (3) Networked interface (online or otherwise) provides a superior, rich customer experience substantially free of requirement(s) to understand/interpret femto AP programming interface or configuration nomenclature. (4) End user(s) can manage (e.g., remove select covered numbers, or add additional numbers for coverage up to an allotted amount for white list(s) associated with the user. (5) Capacity to determined quality of service, grade of service, or service experience, for specific authorized subscribers. (6) Capacity to check for valid wireless device numbers, codes or tokens (e.g., MSISDNs); subscriber's active numbers, codes or tokens; and numbers, codes or tokens on service accounts in good standing; such capacity can be provided through networked access to a subscriber database 260.

White list(s) 220 facilitates management of access to coverage by a femto AP (e.g., femto AP 130). Various illustrative aspects of embodiments based at least in part on a white list concept are discussed next. It is to be noted, notwithstanding, that variations and extensions of such illustrative aspects are possible and are within the scope of the subject embodiments.

Figure 3:
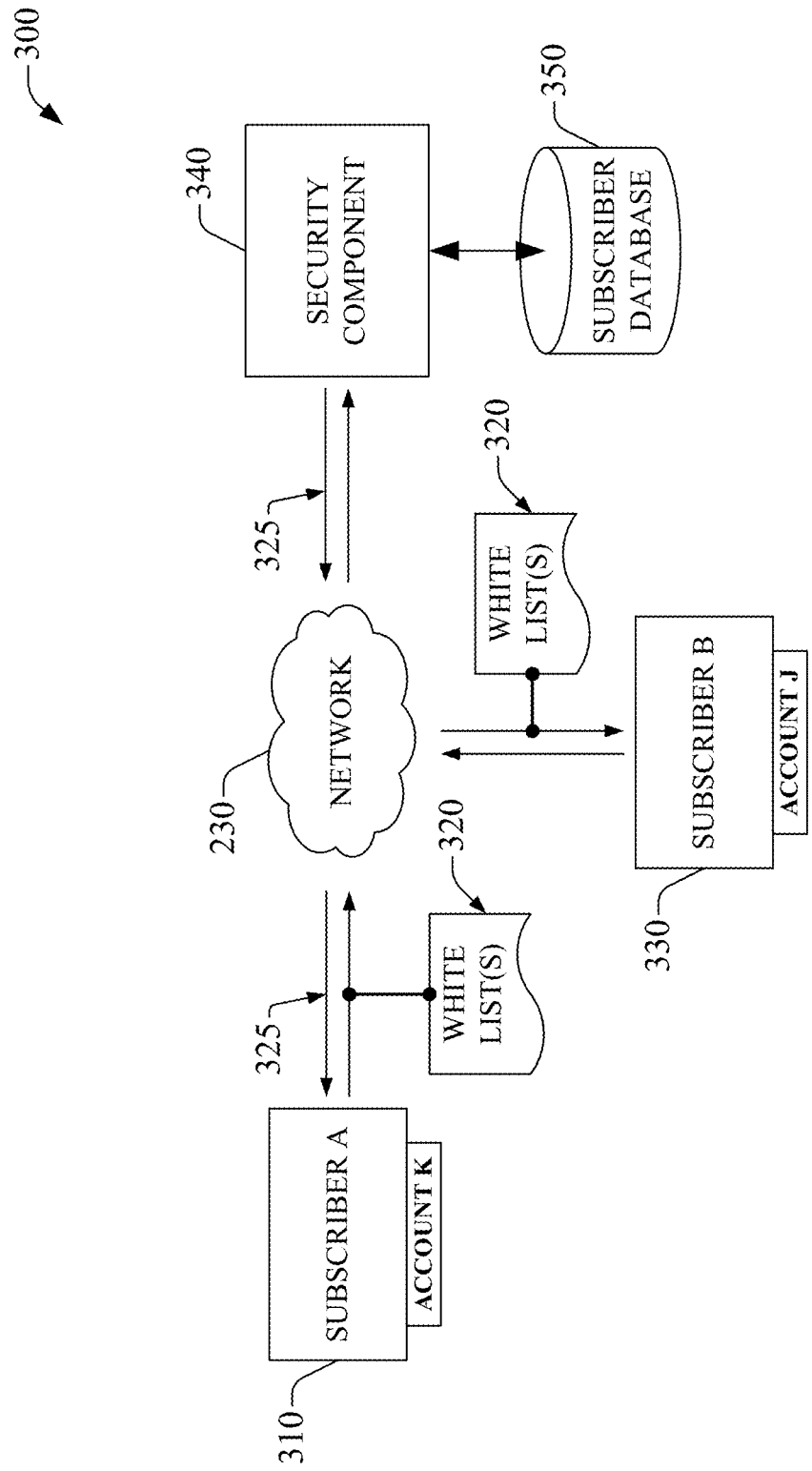
FIG. 3 is a block diagram of an example system to share access control list(s), or white list(s), in accordance with aspects described herein.

FIG. 3 is a block diagram of an example system 300 to share access control list(s), or white list(s) 320, among subscribers of a wireless network service in order to provide straightforward access configuration to, and activation of, a femto cell (e.g., femto AP 130) among femto cell subscribers. Subscribers can belong to disparate or same service accounts with either a macro service provider or femto provide, or both. For example, subscribers that share white list(s) can pertain to a group or family associated with a single service account. In example system 300, subscriber A 310 who belongs to account K conveys white list(s) 320 over network 230, via a wired or wireless link 325, to subscriber B 330 who belongs to account J. Subscriber A 310 can hide or eliminate specific subscriber station numbers from white list(s) 320 he/she/it grants to other subscribers. It should be appreciated that the granting of subscriber station numbers, codes or tokens can substantially reduce the amount of time to configure, or set up a white list, as opposed to manually re-entering multiple (e.g., up to 50 numbers, codes or tokens) across multiple femto cells.

A security component 340, or authorization layer, can ensure that unauthorized mobile subscriber numbers, codes or tokens, are not provided when not approved by end users. Such approval can be determined via a privacy policy associated with the end user, or subscriber, which can be stored in a subscriber database 350; the privacy policy can be configured/updated through various means like web-based interfaces, call center, text-message center, and so on. Security component 340 ensure privacy integrity when white list(s) 320 are shared among subscribers of different accounts (e.g., J≠K). In an illustrative aspect, security component 340 can solicit subscribers outside a "white-list share" originating account to grant the authority for their subscriber station identifier number, code or token to be shared through white list(s). To the latter end, security component 340 can resort to various mechanisms that include, but are not limited to including, a short message service (SMS) communication, a multimedia message service (MMS) communication, email, voice mail, web pop up, and so on. Alternatively, or in addition, security component 340 can mitigate security mechanism(s) complexity through validation via subscriber account information (e.g., stored in subscriber database 350) in order to grant automatic access to white list(s) within groups or families underneath a single service account, without additional security verification.

Figure 4:
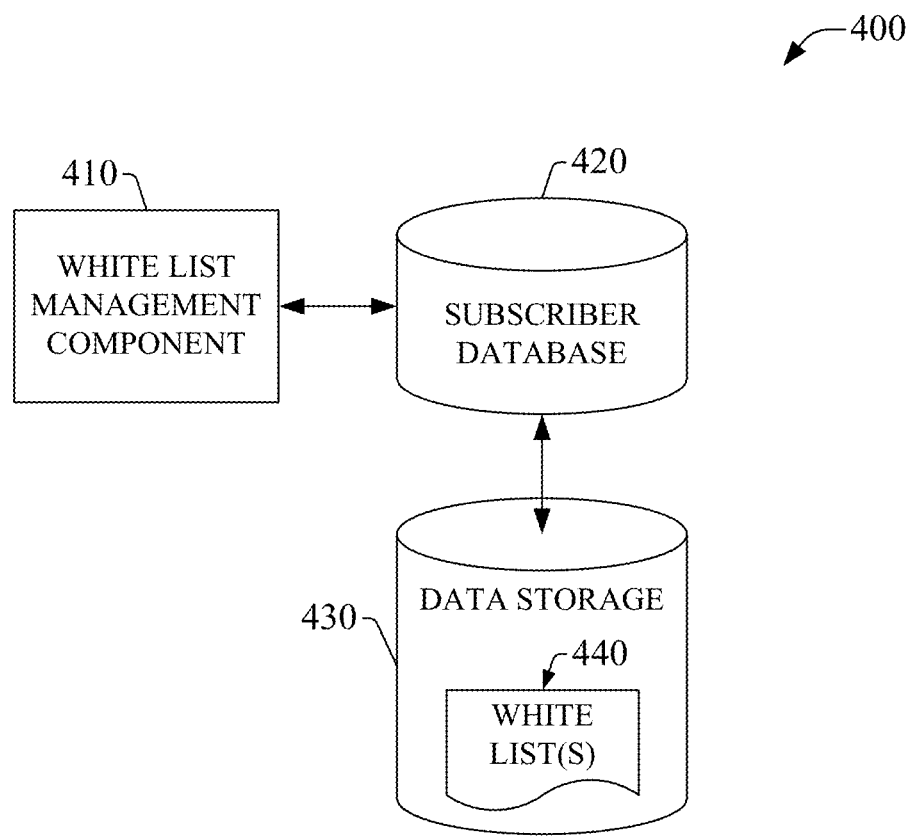
FIG. 4 is a block diagram of an example system that manages access control lists, or white lists, in accordance with aspects described herein.

FIG. 4 is a block diagram of an example system 400 that manages access control lists, or white lists. White list management component 410 accesses a subscriber database 420 which can be maintained by a service operator for femto and macro cells, and a data storage 430 that retains a set of white lists 440 associated with serviced subscribers, to associate white-listed subscribers across disparate access control lists. Such association can lead to genesis of white-lists trees. In an aspect, white list management component can implement mechanisms to mitigate exponential data growth and efficient storage of white-list trees like data-compression (e.g., wavelet, efficient tree representation, and so on), distributed data warehouses, and so forth. In another aspect, white list management component can deploy a white-list tree in accordance to the following illustrative, non-limiting scenario. (i) User 1 adds User 2 to his/her white list. (ii) User 2 adds User 3 to his/her white list. (iii) User 1 and User 3 can be associated through white lists. (iv) User 1 and User 3 can match User 4 extant on each other's white lists. (v) User 1 and User 3 can associate User 5 that is on User 4's white list. White list management component 410 effects associations and manages generated white-list tree(s). It should be appreciated that substantially any association, hierarchical or non-hierarchical, or deployment of white lists can be implemented by white list management component 410 through information stored in subscriber database 420 and data storage 430.

An illustrative, non-limiting, advantage of structured, hierarchical generation of white lists to subscribers (e.g., subscriber A 310) is that more subscribers can have access femto cells to gain coverage enhancement, or have access to added value through unlimited usage on any femto cell or unique services available via a set of femto cells.

In addition, example system 400 can track subscriber station identifier numbers (e.g., MSISDNs), codes or tokens, associated with white list(s) on record with a femto service provider. White list management component 410 can validate white list(s) 440, stored in data storage 430, against current accounts and associated subscriber station identifier numbers (e.g., MSISDNs), codes, or tokens, for a service provider. In particular, when a subscriber, or end user, cancels an account with service provider, white list(s) 440 can be updated according to information retrieved from subscriber database 420, or substantially any other database available to a service provider that contains information on service subscribers. In addition, when an end user changes their mobile or subscriber station number, code or token, (e.g., after relocation to a new area code, or the like) substantially all white list(s) 440 that the mobile or subscriber station number, code or token is associated with can automatically be updated by white list management component 410.

An illustrative advantage of such automatic update of white list(s) 440 is ease of use for end users to maintain current white list(s) 440 without a need to keep track of each subscriber station number, code or token associated with the white list(s) 440. In addition, updated white list(s) 440 maintains the value proposition of the femto cells for end users and service operator by a seamless move of traffic off of the macro network (e.g., a WAN) to femto network(s).

Figure 5:
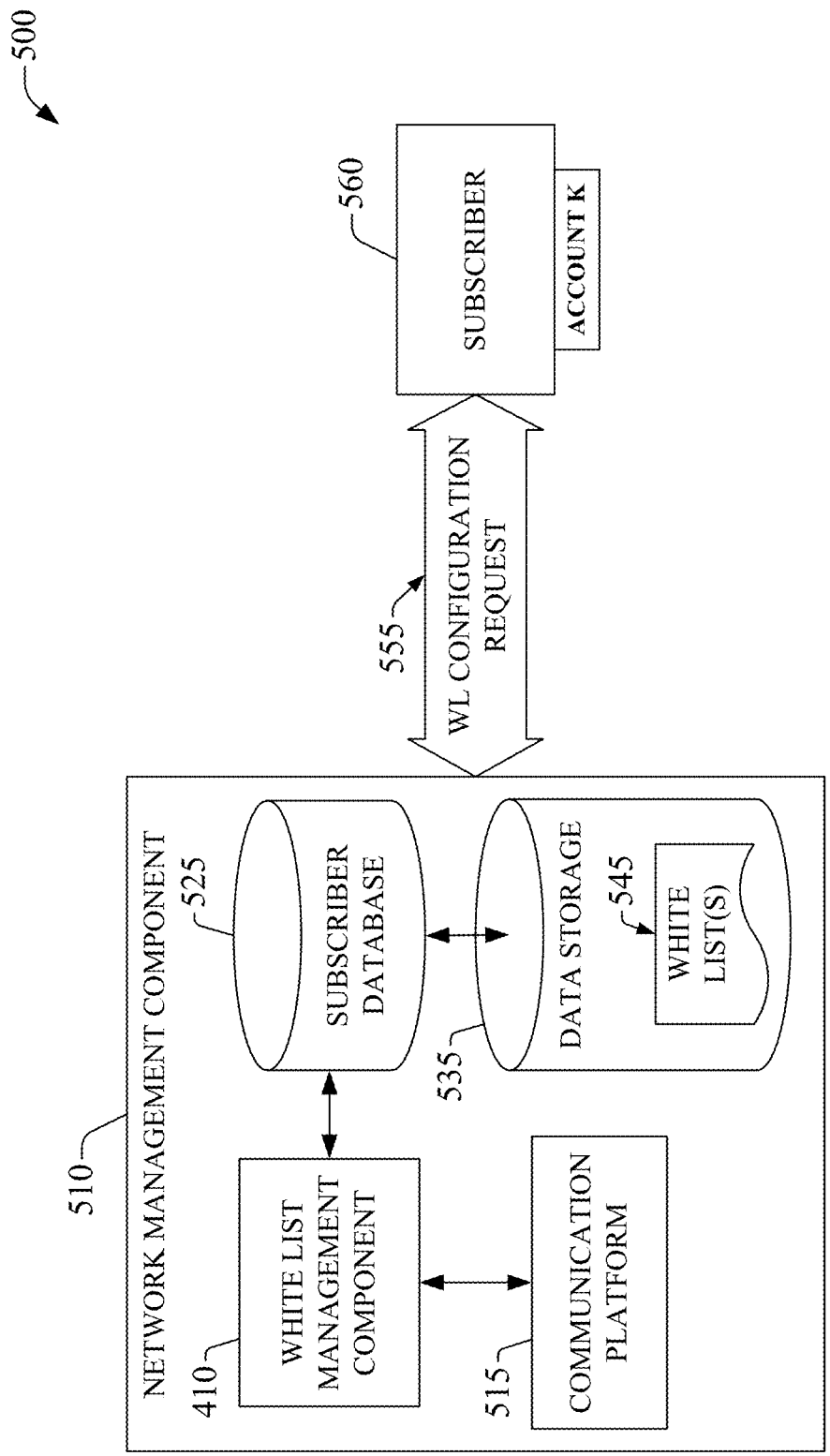
FIG. 5 is a block diagram of an example system that facilitates addition of subscriber(s)/subscriber station(s) to one or more white lists in accordance with aspects described in the subject specification.

FIG. 5 is a block diagram of an example system 500 that facilitates addition of subscriber(s)/subscriber station(s) to one or more white lists. In example system 500, a network management component 510 includes a white list management component 410 which is coupled to a subscriber database 525, a data storage 535 and a communication platform 515. The white list management component 410 can data-mine subscriber database 525 and white list(s) 545, which resides in data storage 535, to drive addition of new subscribers to a white list to request reciprocal adding. In an aspect, once a subscriber 560 in account K is identified for reciprocal addition at a time the subscriber 560 configures his/her femto AP, a white list (WL) configuration request 555 is conveyed (e.g., via a wired or wireless link through communication platform 515) to the subscriber. Such configuration request indicates that a disparate subscriber has subscriber 560 white-listed and prompts subscriber 560 to include in his/her white list the disparate subscriber. An illustrative scenario is the following: User 1 adds User 2 to his/her white list. Once User 2 configures/activates his/her femto cell, a setup process (implemented, for example, through a web-based online GUI) will prompt User 2 to add User 1. It is to be noted that white list management component 410 can exploit information in subscriber database 525 and data storage 535 to inform User 2 of substantially all subscriber station numbers, codes or tokens that he/she can add automatically on a reciprocity basis; namely, User 2 can be prompted to add in white list(s) those subscribers that have previously added him/her to their with list(s). White list configuration request 555 can be effected through various interfaces like an online GUI, a real time prompt/alert delivered via SMS, MMS, email, instant message, and so forth.

Figure 6:
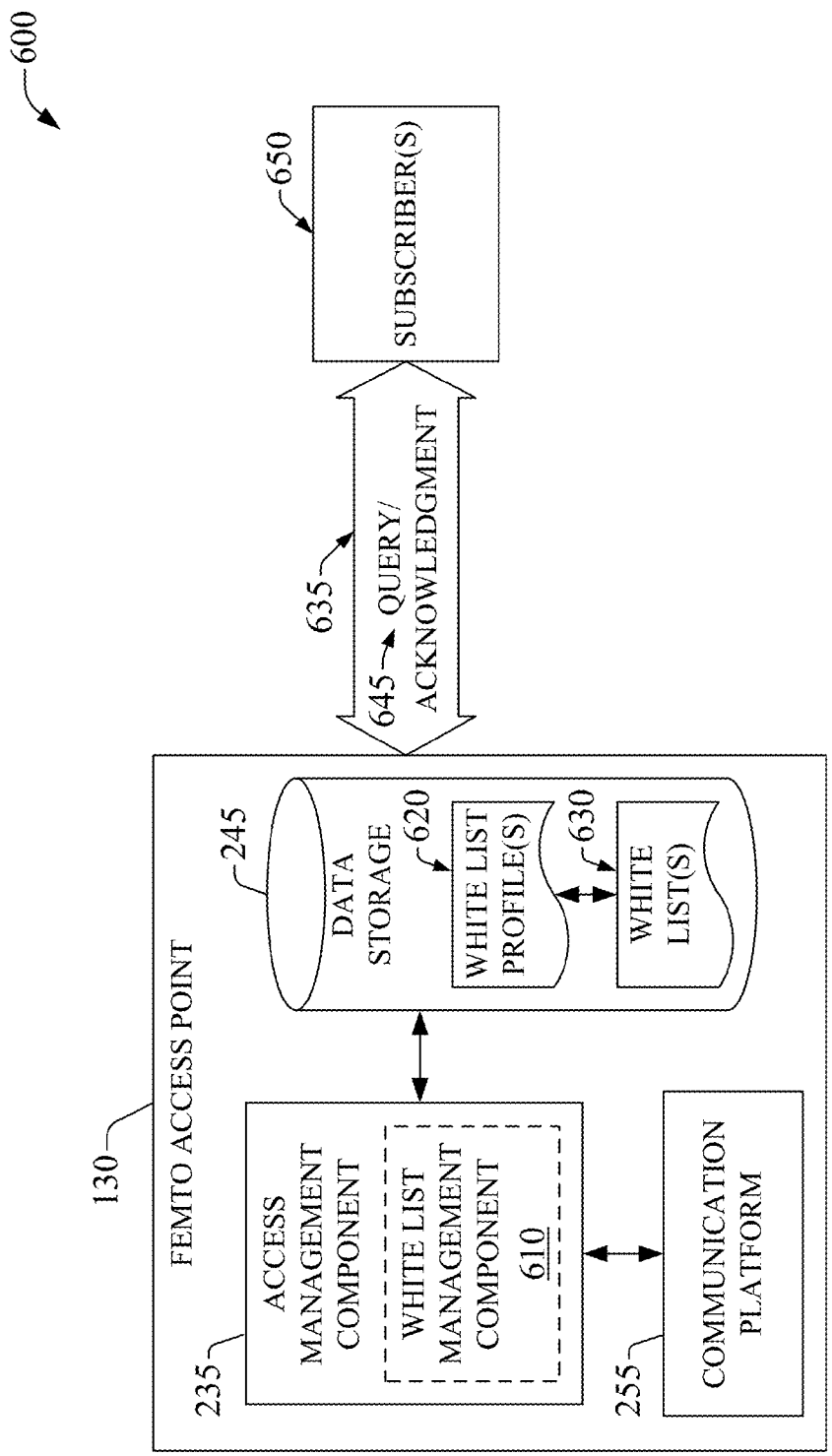
FIG. 6 is a block diagram of an example system that manages a defined logic of how content(s) (e.g., MSISDNs) in access control list(s), or white list(s) is maintained on a white list database in accordance with aspects described herein.

FIG. 6 is a block diagram of an example system that manages a defined logic of how content(s) (e.g., MSISDNs) in access control list(s), or white list(s) is maintained on a white list database. Access management component 235, which can comprise a white list management component 610, can develop white list profile(s) 620 that applies logic and parameters that control, or manage, content in white list(s) 630 such as subscriber station numbers (e.g., MSISDNs), codes or tokens. White list profile(s) 620 and white list(s) 630 can be stored in data storage 615; it should be appreciated that while data storage 245 is illustrated to reside within femto access point 130, such storage can reside in a network management component (e.g., component 510).

In an aspect, white list profile parameters that control utilization logic of white list(s) content include, without being limited to including: (i) temporary access, e.g., full access for a specific time interval such as days or hours; (ii) access only within a window of time in a day (voice and data allowed from 9:00 a-6:00 p, or voice allowed after 9:00 p which can facilitate billing schemes already established by an operator/service provider); and (iii) access to specific applications such as scheduler, calendar(s), news streaming, authoring tools, gaming, video and music, etc.

In another aspect, logic within white list profile(s) can implement parameters to determine how long access to femto coverage is granted. For instance, when a timer associated with temporary access expires, a query 645 can be conveyed (e.g., through a wired or wireless link 635) to either a subscriber that operates a device associated with the managed MSISDN in order to request renewed access, or to a subscriber that operates femto access point 130. The message request, e.g., query 645, can ask the owner if an extension should be granted or not. When a request is not granted by a subscriber that operates femto AP 130 or there is no reply, e.g., acknowledgement 645, from the subscriber, access to femto coverage expires and the MSISDN (or substantially any identifier code or token) is deleted from a corresponding white list(s) within data storage 245. Conversely, a positive response, e.g., acknowledgement 645, can allow access to continue based on either parameters extant in white list profile(s) or newly defined parameters. It is to be noted that query 645 can be conveyed via an online GUI, an email message, a SMS message, MMS message, a voice mail, a web prompt, and the like.

Figure 7:
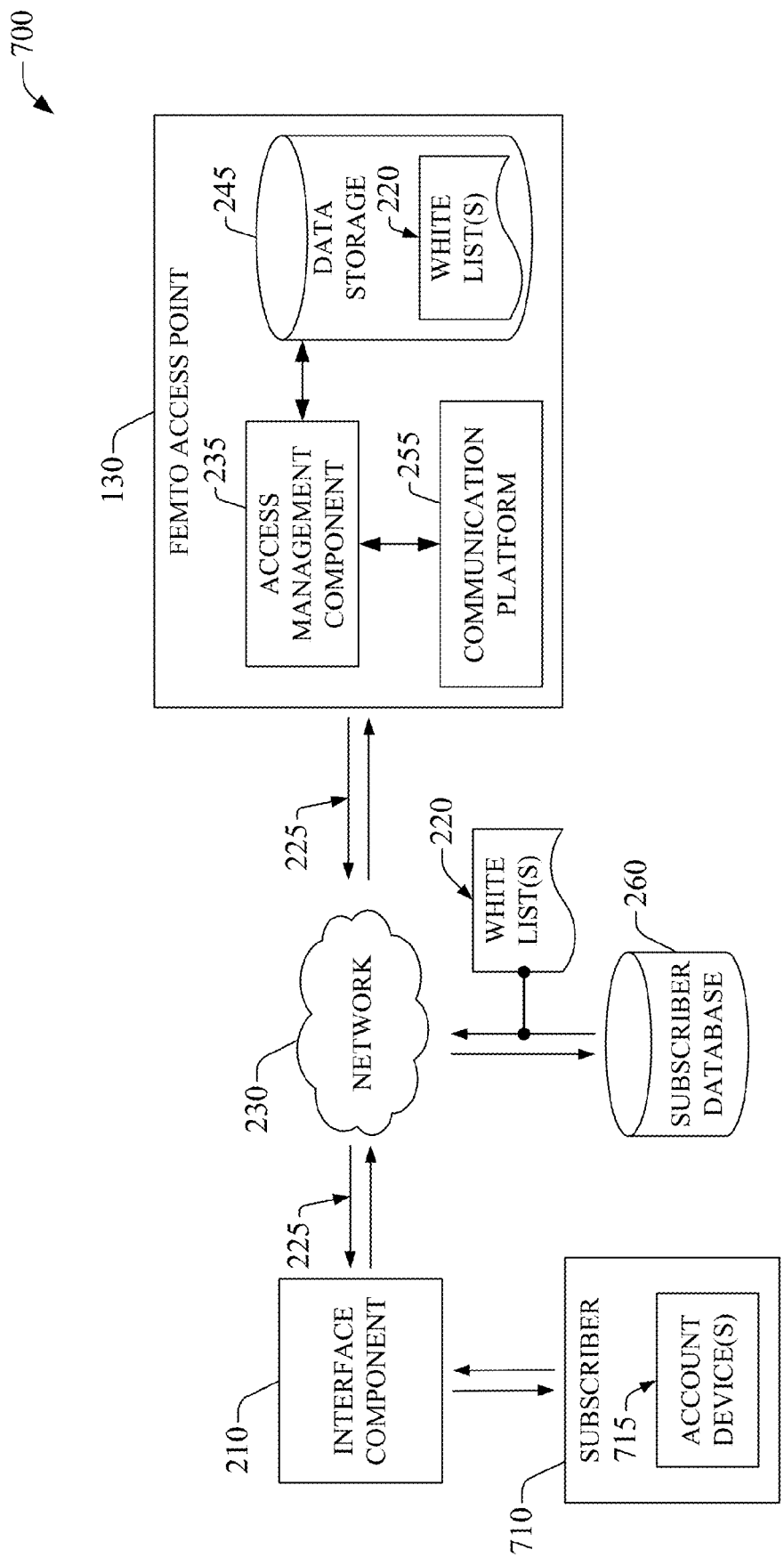
FIG. 7 is a block diagram of an example system that initializes access control list(s), or white list(s), to femto coverage with subscriber station identifier numbers, codes or tokens available on a service account in accordance with aspects disclosed herein.

FIG. 7 is a block diagram of an example system 700 that initializes access control list(s), or white list(s), to femto coverage with available subscriber station identifier numbers, codes or tokens available on a service account. In example system 700, a subscriber 710 who utilizes device(s) 715, can provision femto AP 130 and associate the device(s) 715 with a service account via a networked interface component 210 (e.g., an online account management system) which can look up into substantially all subscriber station(s) identifier numbers (e.g., MSISDNs), codes or tokens associated with the service account, and automatically populates white list(s) 220 with the extracted subscriber station(s) numbers, codes or tokens. Subscriber 710, via interface component 210, can remove or add subscriber station(s) numbers (e.g., MSISDNs), codes or tokens extant in a pre-populated white list(s) 220; additional edits can be performed as well, based at least in part on the complexity of white list(s) 220. In an aspect, to pre-set white list(s) 220, networked interface component 210 access information stored in subscriber database 260 through network 230 which can include information technology systems of a service provider. White list(s) 220 is conveyed through network 230 to femto access point 130; a communication platform receives white list(s) 220 and access management component 235 stores the white list(s) 220 in data storage 245.

An illustrative advantages provided by example system 700 are (a) reduced femto cell provisioning lead time, and (b) immediate utilization of a femto cell with mobile numbers that belong to a same service account, whether subscribers of such numbers subscribe to the femto cell or a feature application, or code, that delivers a femto cell service.

Figure 8:
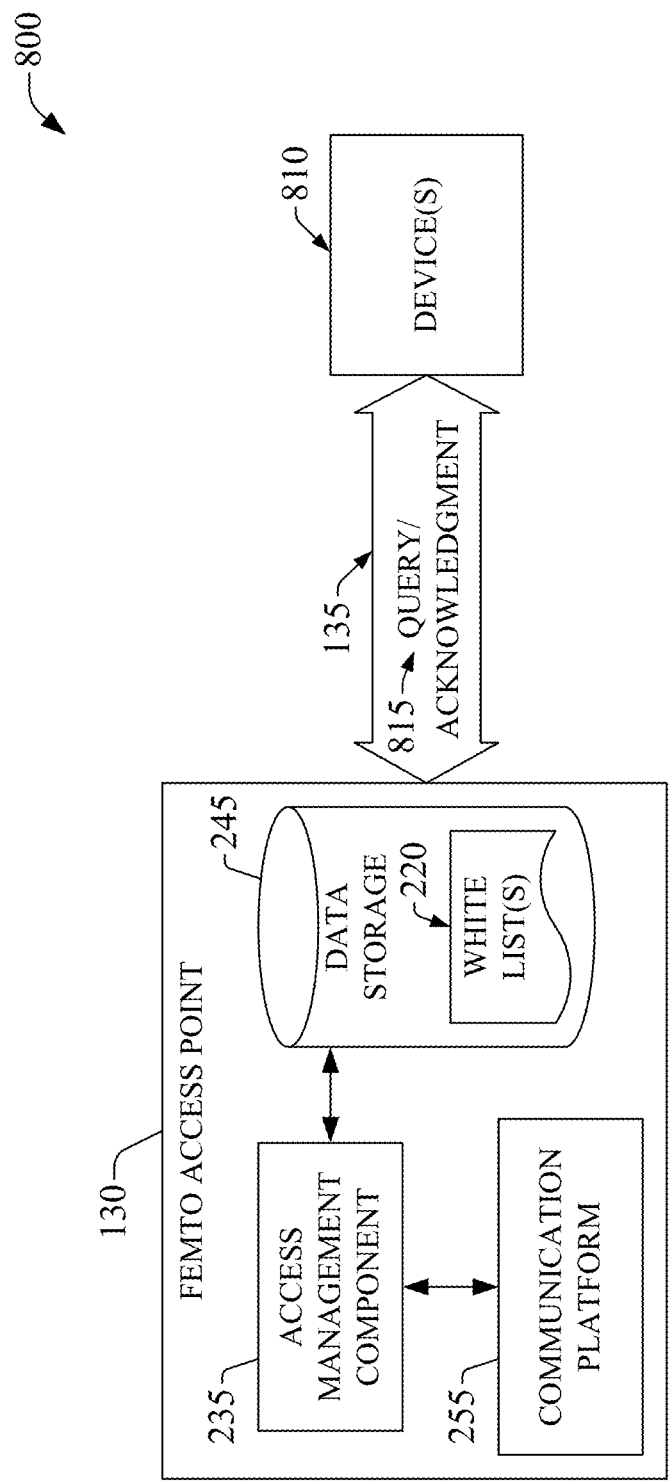
FIG. 8 is a block diagram of an example system that facilitates addition of wireless, mobile devices on an ad hoc basis in accordance with aspects described herein.

FIG. 8 is a block diagram of an example system 800 that facilitates addition of wireless, mobile devices on an ad hoc basis. In example system 800, device(s) 810 can convey a request or query 815 to access coverage of femto AP 130. Such a request can be received by communication platform 255, and access management component 235 can be set up to allow or reject the request; allowance of rejection of a request can be based on various metrics, such as security, type of device, profile of subscriber that operated the device that requests access, and so on. Upon allowance of a request, access management component 235 can query for available slots to be filled in white list(s) 220 associated with accounts served by femto AP 130, when space is available for a subscriber station identifier number (e.g., MSISDN), code or token, the query can further probe whether access is allowed on a permanent, or temporary basis (e.g., to reduce risk exposure to security problems). Characteristics of femto coverage allowance can be set or pre-set through access management component 225. Subsequent to allowance and examination of information related to relevant white list(s) 220, access management component 235 updates white list(s) 220, stored in data storage 245, to reflect the approved request for femto coverage. It is to be noted that access and update of collected subscriber identifier numbers (e.g., MSISDN), codes or token, can also be effected through network-based white list database(s). It is to be noted that query 815 can be conveyed via an online GUI, an email message, a SMS message, MMS message, a voice mail, a web prompt, USSD (or * and # codes), and the like.

An illustrative, non-limiting advantage of example system 800 is that it provides an enhanced end user experience with a direct, clear mechanism and thus encourages use of the femto access point 130, and avoids time spent on edition of white list(s) through a networked interface (interface component 210) like an online interface which takes time for the end user to have access to the Internet, and to log on in a secured interface.

It should be appreciated that substantially any wireless device within coverage area of femto AP 130 (e.g., are 125) can request access without intervention by a subscriber that operates femto AP 130, and who has previously entered a set of subscriber station numbers (e.g., MSISDNs), codes or tokens, via a networked interface (e.g., interface component 210). Alternatively, or in addition, a request for access can be prompted by a device utilized by a subscriber that operates the femto AP. Further a request for access can be effected by the femto AP, through an access management component like component 225, for example. Once a request is granted, a secure tunnel can be established from the device/client through the femto cell's IP connection or the default of the Radio Access Network if the IP connection is not available. Secure layers including utilizing the femto cell's VPN and/or USSD would ensure that the transaction is in fact secure. As a non-limiting example, a temporary visitor or employee (e.g., a babysitter) who is coming over to a location served by a femto access point (e.g., femto AP 130) for a limited period of time, can be provided with coverage via the femto AP by a subscriber that operates the femto cell so the employee can perform, at least in part, his work activities (e.g., provide updates on behavior of children) through utilization of the femto access point. In case the subscriber fails to know identifier numbers, codes or tokens for devices the employee can utilize, and the subscriber is not interested to go through the process of requesting and entering the numbers, codes or tokens via a networked interface to allow coverage for the limited period of time the employee performs work, the employee (e.g., babysitter) can convey a request (e.g., query 815) invention allows the baby sitter to request femto access directly from the employee's device when in range of the femto access point.

Figure 9:
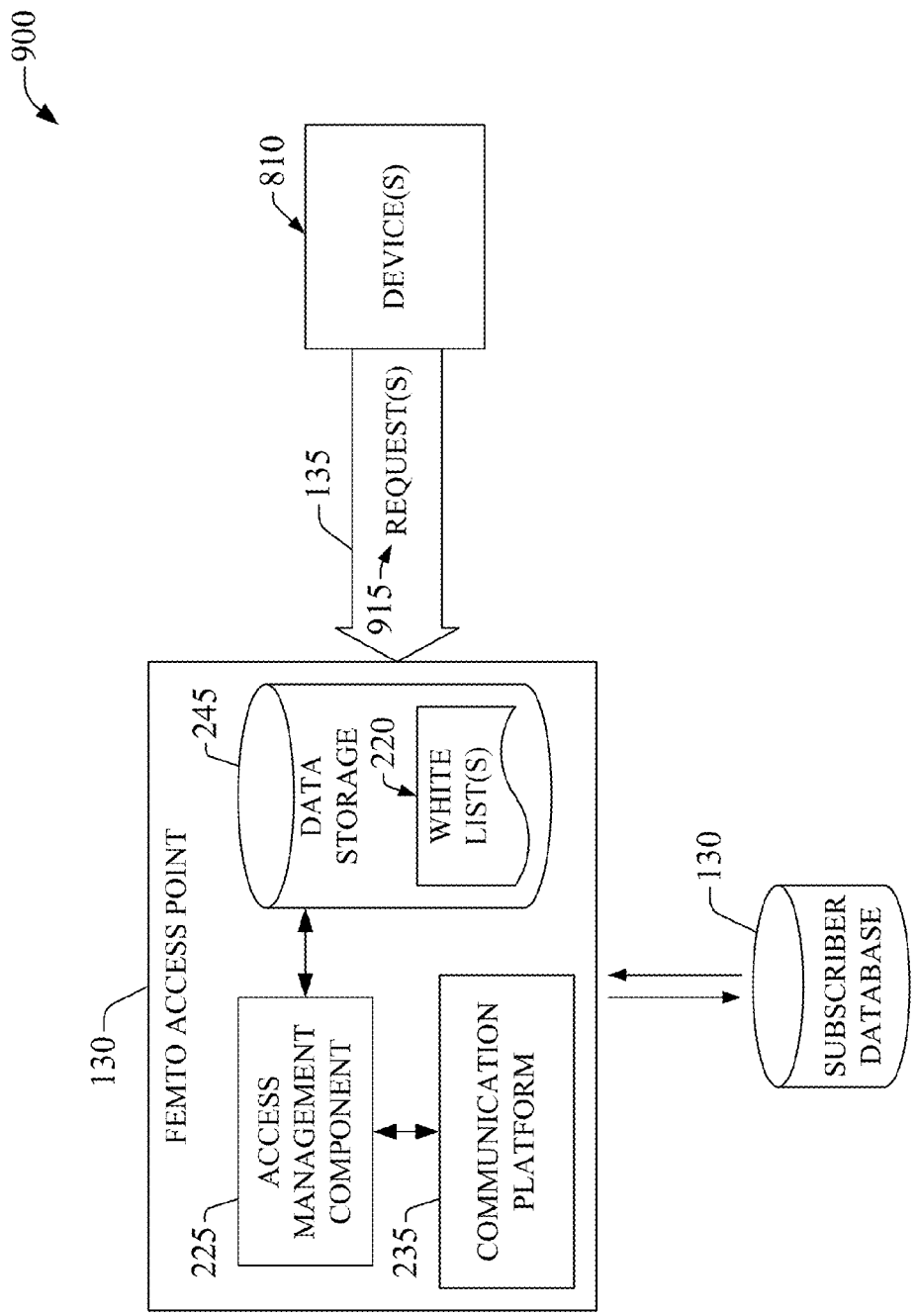
FIG. 9 is a block diagram of an example system that tracks subscriber station identifier numbers (e.g., MSISDNs), codes or tokens, associated with white list(s) on record with a femto service provider in accordance with aspects of the disclosed subject matter.

FIG. 9 is a block diagram of an example system that tracks subscriber station identifier numbers (e.g., MSISDNs), codes or tokens, associated with white list(s) on record with a femto service provider in accordance with aspects of the disclosed subject matter. In accordance with this aspect, device(s) 810 can convey a number change update request 915 to AP 130. Upon receiving such a request at the communication platform 255, the white lists 220 can be updated accordingly. The white lists can also be updated to reflect any changes that users may make to their services providers such as changing a service provider or canceling service etc. Hence, when an end user changes their mobile number (e.g. moving to a new area code, etc.) all white lists 220 that the mobile number is associated with will automatically be updated upon receiving the request. Therefore, it enables the communication system 900 to keep track of MSISDNs associated with the white lists 220 on record and validates the white lists against current user accounts and MSISDNs associated therewith. This provides ease of use to a user associated with administering the femto cell as it aids in maintaining current white lists without having to keep track of each mobile number associated with the white list. Additionally, it maintains value proposition of the femtocells for end users and a cellular operator by continuing to move traffic off of the WAN to the femtocell in a seamless fashion.

Figure 10:
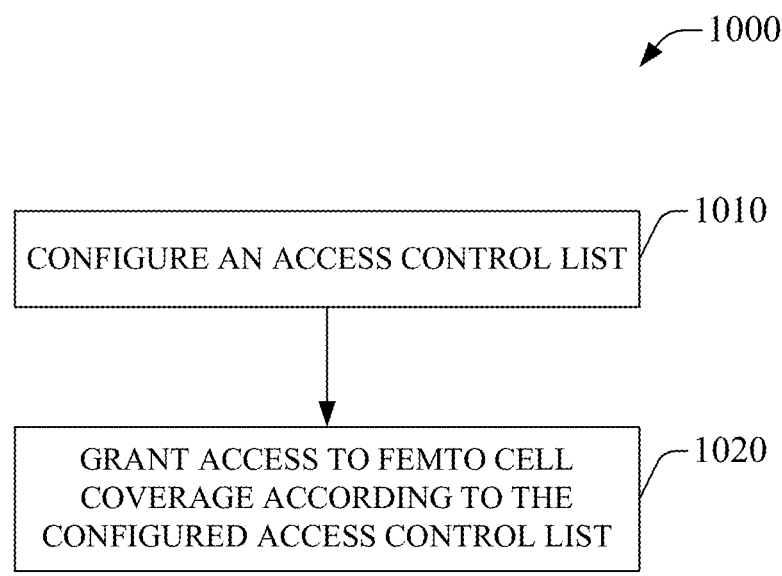
FIG. 10 presents a flowchart of an example method for managing access of subscribers and subscriber stations to femto cell coverage according to the disclosed subject matter.

In view of the example systems described above, example methodologies that can be implemented in accordance with the disclosed subject matter can be better appreciated with reference to flowchart in FIG. 10. For purposes of simplicity of explanation example method 200 is presented and described as a series of acts; however, it is to be understood and appreciated that the claimed subject matter is not limited by the order of acts, as some acts may occur in different orders and/or concurrently with other acts from that shown and described herein. For example, those skilled in the art will understand and appreciate that a methodology could alternatively be represented as a series of interrelated states or events, such as in a state diagram, or interaction diagram. Moreover, not all illustrated acts may be required to implement a methodology in accordance with the subject specification. Additionally, it should be further appreciated that the methodologies disclosed hereinafter and throughout this specification are capable of being stored on an article of manufacture to facilitate transporting and transferring such methodologies to computers for execution by a processor or for storage in a memory.

FIG. 10 presents a flowchart of an example method 1000 for managing access of subscribers and subscriber stations to femto cell coverage. At act 1010 an access control list, or white list, for a femto cell is configured. In an aspect, configuration can be performed via a networked interface, interactively or automatically based at least in part on operation conditions of the femto cell; e.g., initial provisioning, capturing of wireless devices, responding to request for access, updating extant access control lists, and so forth. At act 1020, access to femto cell coverage is granted according to the configured access control list. In another aspect, the configured access control list can possess an associated profile that control logic for utilization of the access control list, via a set of parameters that determine conditions of access, type of access, etc. Additional aspects of example method 1000 can be enacted through example methodologies presented in flowcharts detailed infra.

Figure 11:
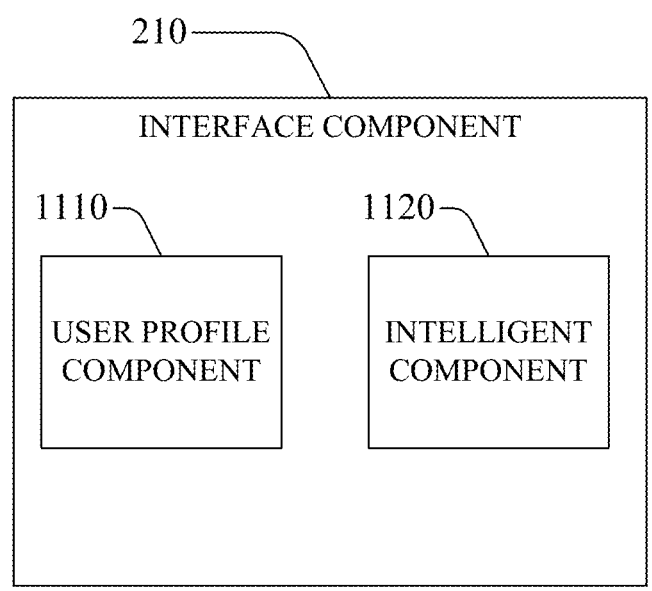
FIG. 11 is a schematic diagram of an interface component that can be used to mange one or more white lists associated with a femto access point.

FIG. 11 is a schematic diagram of an interface component that can be used to mange one or more white lists associated with a femto cell. In accordance with an aspect, within an object oriented environment, an interface can contain methods (both class and instance), static fields, properties and events in order to execute the functionality associated there with. The interface component 210 can comprise a user profile component 1110 and an intelligent component 1120. The user profile component 1110 is configured to store profiles of users who operate or administer the femto cell associated there with. Each of the users can be associated with a different status thereby causing a differentiation in their respective administrative rights/responsibilities. Thus, the user profile component 1110 comprised in the interface component 210 can aid in providing an appropriate interface based at least on a user's profile. For example, a GUI presented to a user logged in as a primary administrator can be different compared to an interface presented to a secondary user with limited administrative rights to the femto cell. In a further aspect, the secondary user can be permitted to grant only temporary access to a requesting UE and hence an abbreviated interface can be presented to such a secondary user as compared to a richer interface presented to the primary administrator.

As described supra, various kinds of interfaces such as a web-based GUI or an interface responsive to touch screen or voice commands can be presented. This can be based on an input from the user profile component 1110 or the intelligent component 1120. For example, if the user profile component 1110 indicates that the user is a new user or if the intelligent component indicates a task such as addition or deletion of a number from the white lists 220 then the interface can be a wizard type interface that guides the user through a specific task via a question/answer session. The intelligent component 1120 can also aid in presenting an interface appropriate for a given device. Various aspects can be considered while selecting a device on which the interface can be presented. For example, if the user requests the interface by logging into the user account, then the device from which the user has logged in can be sensed by the intelligent component and an appropriate interface can be presented. If the user is logging in from a mobile device such as a cell phone/PDA (personal digital assistant) etc. then a simple interface with minimum graphics can be provided. If it is sensed that the user is logging in from a laptop computer, then a more complex interface can be presented.

As mentioned supra, when a subscriber station, e.g., a UE leaves macro coverage and enters femto coverage, it attempts to attach to the femto AP through transmission and reception of attachment signaling, effected via a FL/RL. In accordance with an aspect, it can be verified if the UE attempting to access the femto cell resources is included in the associated white list. If yes, then the UE is granted femto coverage else, the intelligent component 1120 can automatically present a simple/abbreviated interface to the user providing the user with an option to grant or deny the UE access to the femto cell resources. In a further aspect, the intelligent component 1120 can be configured to automatically present an appropriate interface at a device that is either specified by the user or a device that is inferred as being at the focus of the user's attention. For example, if the default device configured by a user to receive notifications associated with the white list management is powered off, then the intelligent component 1120 can select and present an appropriate interface at an alternate device that it infers as being at the focus of the user's attention. If there are multiple devices that are likely to have the user's attention, then a confidence threshold can be employed to select a device that is most likely to be at the focus of the user's attention. Additionally, the access rights granted to the UE can vary based on the kind of interface from which its access to the femto resource has been approved. The intelligent component 1120 can be configured to communicate with the access management component 235 in order to determine the kind of access that can be granted to a requesting UE.

Figure 12:
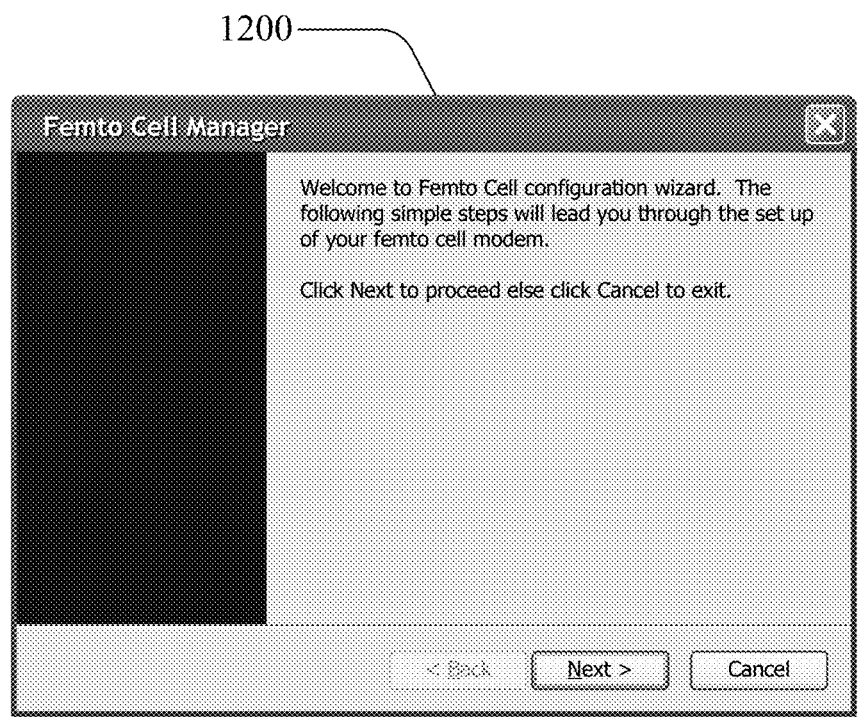
FIG. 12 illustrates a GUI that can be employed by users to configure the femto access point and manage various aspects associated with the femto cell access.

In accordance with an aspect illustrated in FIG. 12, a GUI 1200 can be employed by users to configure the femto AP and manage various aspects associated with the femto cell access. In particular the interface 1200 can be presented to a user when the femto access point is initially plugged into the system. Upon start up of the system, the initial welcome screen 1200 of a configuration wizard is presented that will guide the user through the set up and configuration of the femto access point. Further screens (not shown) can allow the user to input system parameters and generate initial white lists by allowing the user to add subscriber station numbers (e.g., MSISDNs). However, further addition, deletion and/or editing of white list contents through other interfaces is possible as detailed infra.

Figure 13:
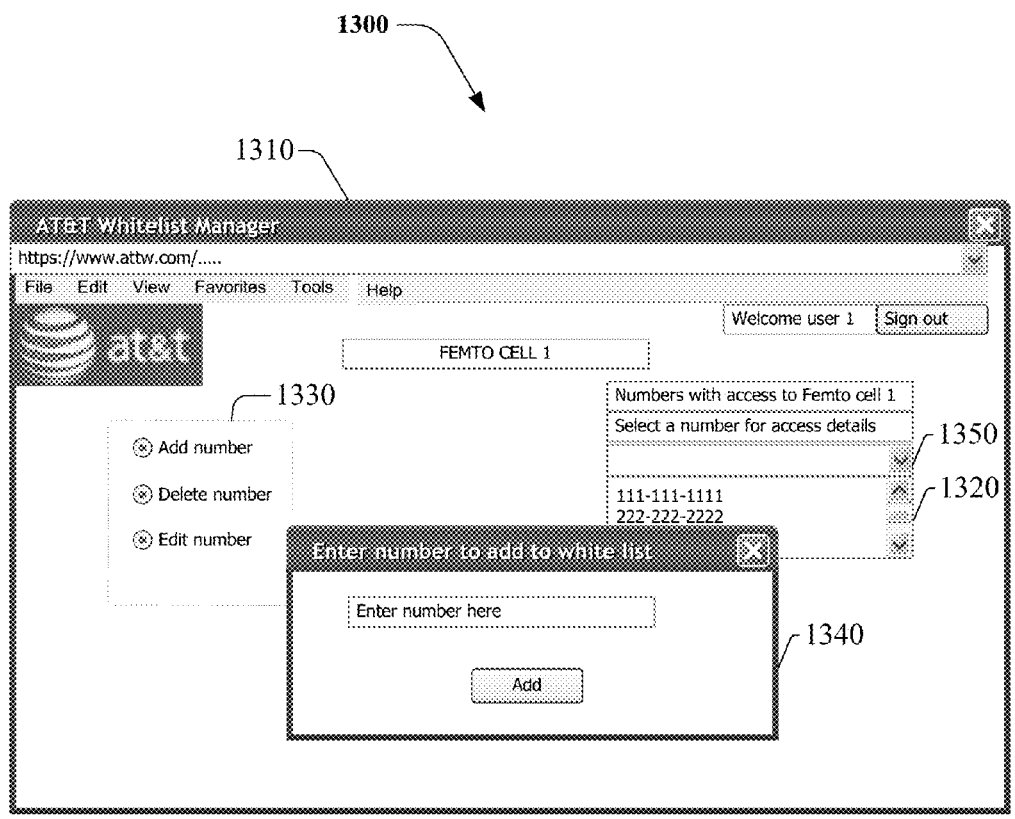
FIG. 13 shows a web based GUI that can be employed by the user to edit contents of a white list upon installation of the femto access point.

FIG. 13 shows a web based GUI 1300 that can be employed by the user to edit contents of a white list upon installation of the femto access point. A user can log in to an online account to control the femto cell access. A screen 1310 can be presented to the user upon logging into the online account. It can comprise a list of IDs 1320 that currently have access to femto cell resources. It should be noted that the format is shown as a means of illustration and not limitation. Various other formats can be employed to show the users/UEs that have access to the femto cell resources. For example, user names associated with the MSISDNs or other tokens can be used in the list. In another aspect, the list can show all IDs associated with UEs that not only have current access but previously had access to the femto resources. Selection of a specific ID from the list can show the access details associated with the ID. For example, the access details gathered from the associated white list profiles can include if the selected ID currently has access to the femto cell resources, or if the particular ID previously had access, details such as the time, date and/or the period of access can be shown.

A group of options 1330 allow a user to manipulate contents of the white list 1320. By the way of illustration and not limitation, the options can include an option to add IDs to the list, an option to delete IDs from the list and an option to edit existing IDs in the list. Upon selection of an option by a user, further dialog can be conducted with the user to continue with the selected task. For example, if the user chooses to add numbers to the white list 1320, a pop up window 1340 can be presented to collect the details of the ID to be added to the white list 1320. In another aspect, an ID selected from the list 1320 can be displayed in the box 1350 to facilitate editing the selected ID. However, as discussed supra, various alternate devices can be used to present the interface that facilitates editing a white list.

Figure 14:
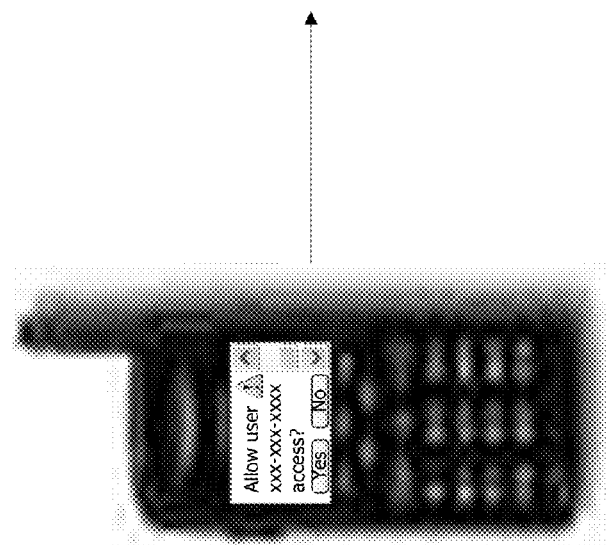
FIG. 14 A and FIG. 14 B illustrate different devices presenting the interface in accordance with different aspects.
Figure 14:
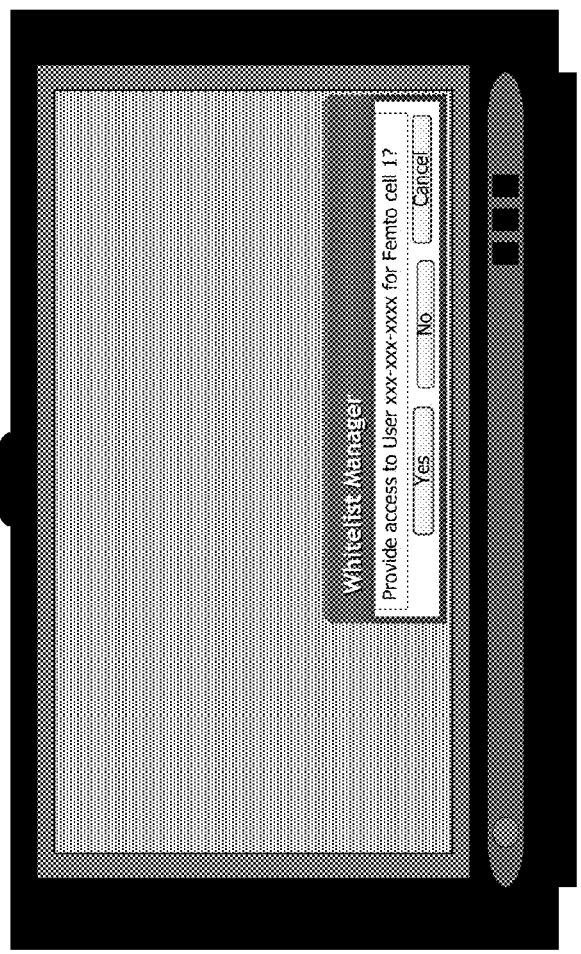

FIG. 14 A and FIG. 14 B illustrate an aspect wherein the interface is presented on different devices. In FIG. 14 A, the interface 1410 is presented in the television 1400. Accordingly, it can be a simple or an abbreviated interface in accordance with users' convenience. Presenting more abbreviated interfaces on secondary devices mitigates the need for the user to spend time and attention to the task of allowing/denying access rights to a requesting UE thereby allowing them to continue with whatever task they may be currently engaged in. Accordingly, an ID associated with a UE attempting to access the femto resources is used to request permission for the same. Thus, a remote control associated with the television set can be operable to select one of the YES/NO option buttons thereby granting/denying access thereby quickly concluding the task of editing the white list. As mentioned supra, in accordance with this aspect, the kind of permission granted to the UE can vary based on a type of device/interface granting the access. If a simple interface is granting access, then a temporary access can be granted wherein a timer can be associated with the temporary permission granted to the UE. A further query can be directed to the user upon expiration of the time period associated with the access in order to extend the access period.

Similarly FIG. 14 B illustrates an aspect wherein the interface 1420 is presented on a user's cellular telephone 1430. It can be appreciated that although the figures illustrate a television and a cellular phone only, the user interfaces can be presented on one or more other devices such as a, a PDA and/or a laptop computer etc.

Figure 15:
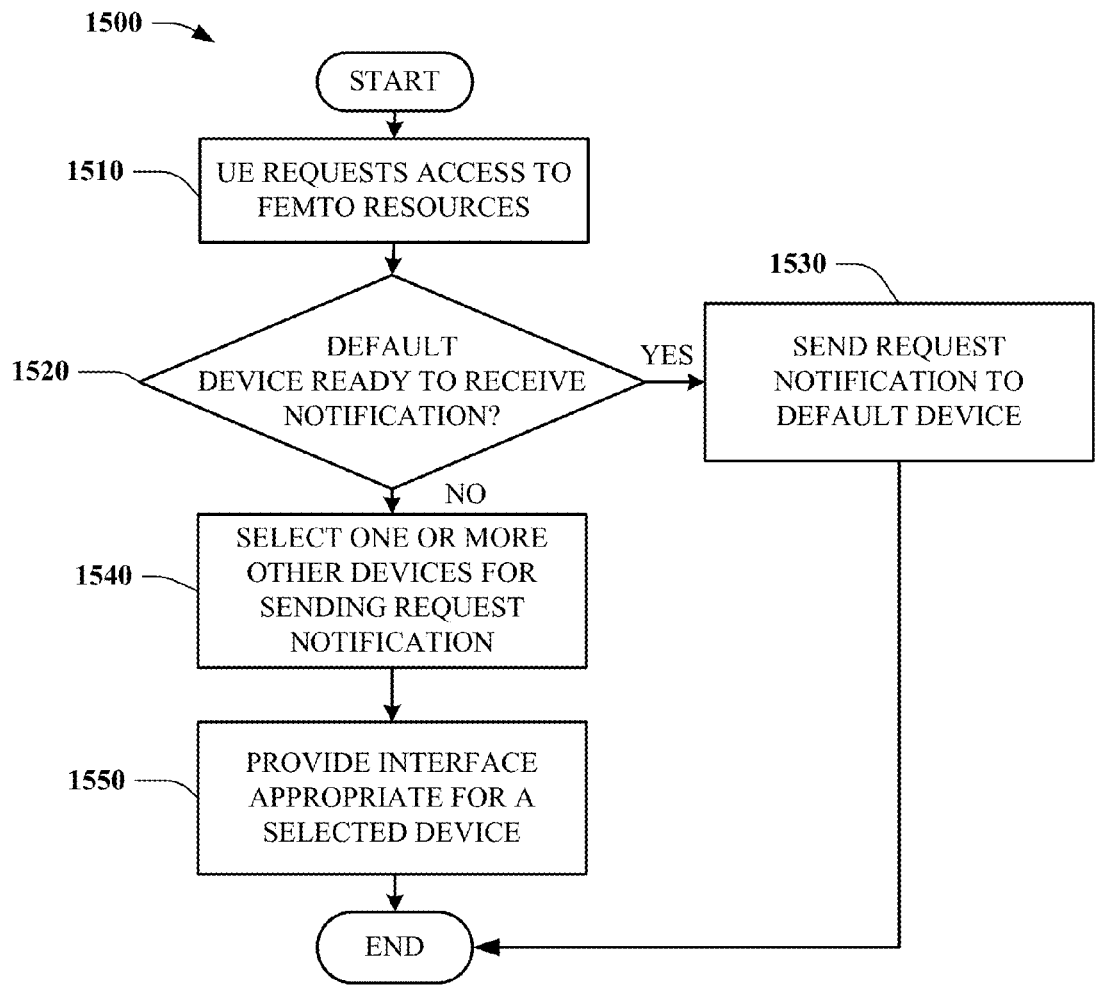
FIG. 15 shows a methodology of providing white list management interface to a user in accordance with an aspect.

FIG. 15 shows a methodology of providing white list management interface to a user in accordance with an aspect. The method 1500 begins at 1510 with a UE requesting access to femto cell resources. The method proceeds to 1520 wherein it is verified if a specified default device is ready to provide the request notification/message to the user. If yes, then a message specifying the ID of the requesting UE is provided to the user with options to grant or deny access as shown at 1530. If at 1520, it is determined that the default device is not ready to provide messages to the user, the method then proceeds to 1540 wherein one or more secondary devices are selected for providing notifications. For example, if the default device is not powered on then it will not be ready to provide resource request messages to the user. Accordingly, an interface appropriate for the selected secondary device can be provided at the one or more other devices as shown at 1550. The selection of the other devices can be based on one or more of user choices and/or confidence thresholds associated with such alternate devices. The confidence thresholds for selecting other devices can be estimated based on one or more of a time of the day, status of the devices, user options etc.

Figure 16:
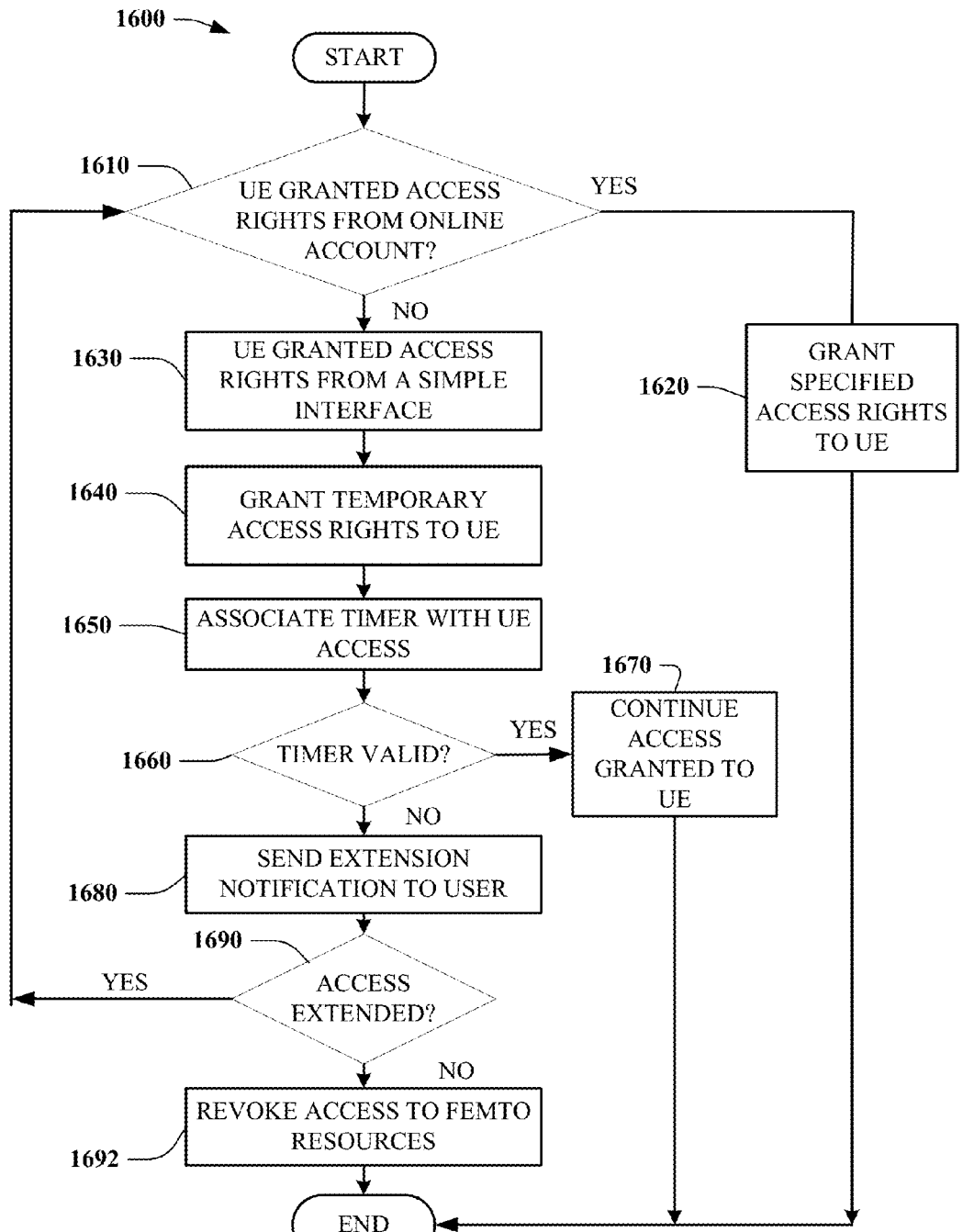
FIG. 16 relates to another aspect wherein the access rights granted to a UE can depend on the kind of interface that is used to grant the access rights.

FIG. 16 relates to another aspect wherein the access rights granted to a UE can depend on the kind of interface that is used to grant the rights. The method 1600 of granting access rights can begin at 1610 wherein it is verified if the UE has been granted access rights from an online account. If yes, then the access rights as specified can be granted to the UE as shown at 1620. As detailed supra, various kinds of access can be provided to a UE. For example the UE can be granted permanent access rights by including the UE into the white list. In accordance with other aspects, the access rights of a UE can be associated with a timer such that when the specified time period expires the UE access to the femto cell resources also expire unless explicitly extended by a user. If it is determined at 1610 that the access rights were not granted from an online account, it is determined at 1630 that the UE was granted access from a simpler interface. Accordingly, the UE can be granted temporary access rights as shown at 1640. Hence, a timer can be associated with the access rights granted to the UE as shown at 1650. In a further aspect, the timer can have a default time period associated there with for granting access rights. Such a default time period can be set by the user, for example, during the initial configuration of the femto access point. At 1660, it is verified if the timer has expired. If the timer is not yet expired, the UE continues to have the temporary access rights as how at 1670 unless explicitly changed by the user, for example, from the online account. If it is determined at 1660 that the timer has expired, a message is sent to the user requesting further user action regarding extension of the UE access rights as shown at 1680. At 1690 it is determined if the user extended the access rights. If yes, the method returns to 1610 wherein the access rights are granted based at least on the type of interface granting the rights else the access rights are revoked as show at 1692.

Figure 17:
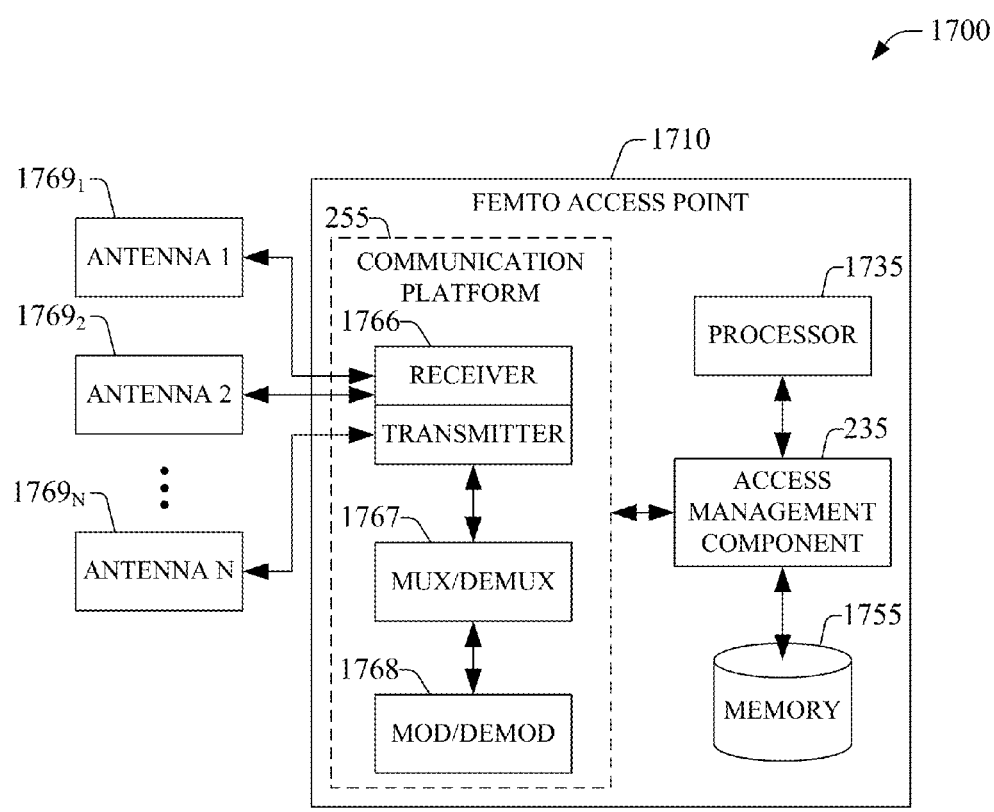
FIG. 17 is a block diagram of an example femto access point that operates in accordance with aspects disclosed in the subject specification.

To provide further context for various aspects of the subject specification, FIG. 17 is intended delineate a suitable wireless communication environment, and associated components, for operation of a femto cell (e.g., femto cell 125) in accordance with various aspects of the specification. In addition, FIG. 17 illustrates a block diagram of an example embodiment 1700 of a femto access point that can enable and exploit and manage femto coverage via access control list(s), or white list(s), in accordance with aspects described herein. Those skilled in the art will recognize that the specification also be implemented through program modules stored in a memory and executed by a processor, and/or other combination of hardware and software.

With respect to FIG. 17, in embodiment 1700, femto AP 1710 can receive and transmit signal(s) from and to wireless devices like macro and femto access points, access terminals, wireless ports and routers, and the like, through a set of antennas $1769_1$-$1769_N$. It should be appreciated that while antennas $1769_1$-$1769_N$ are a part of communication platform 255, which comprises electronic components and associated circuitry that provides for processing and manipulation of received signal(s) and signal(s) to be transmitted. In an aspect, communication platform 255 includes a receiver/transmitter 1766 that can convert signal from analog to digital upon reception, and from digital to analog upon transmission. In addition, receiver/transmitter 1766 can divide a single data stream into multiple, parallel data streams, or perform the reciprocal operation. Coupled to receiver/transmitter 1766 is a multiplexer/demultiplexer 1767 that facilitates manipulation of signal in time and frequency space. Electronic component 1767 can multiplex information (data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1767 can scramble and spread information (e.g., codes) according to substantially any code known in the art; e.g., Hadamard-Walsh codes, Baker codes, Kasami codes, polyphase codes, and so on. A modulator/demodulator 1768 is also a part of operational group 1725, and can modulate information according to multiple modulation techniques, such as frequency modulation, amplitude modulation (e.g., M-ary quadrature amplitude modulation (QAM), with M a positive integer), phase-shift keying (PSK), and the like.

Femto access point 1710 also includes a processor 1735 configured to confer functionality, at least partially, to substantially any electronic component in the femto access point 1710. In particular, processor 1735 can facilitate access management component 235 to supply fixed differentiated QoS in accordance to aspects disclosed herein. In addition, processor 1735 can facilitate operations on data (e.g., symbols, bits, or chips) for multiplexing/demultiplexing, such as effecting direct and inverse fast Fourier transforms, selection of modulation rates, selection of data packet formats, inter-packet times, etc. A memory 1755 can store data structures, code instructions, system or device information like policies and specifications, code sequences for scrambling, spreading and pilot transmission, floor plan configuration, access point deployment and frequency plans, scheduling policies, and so on.

In embodiment 1700, processor 1734 is coupled to the memory 1755 in order to store and retrieve information necessary to operate and/or confer functionality to communication platform 255, access management component 235, and other operational aspects of femto access point 1710.

Figure 18:
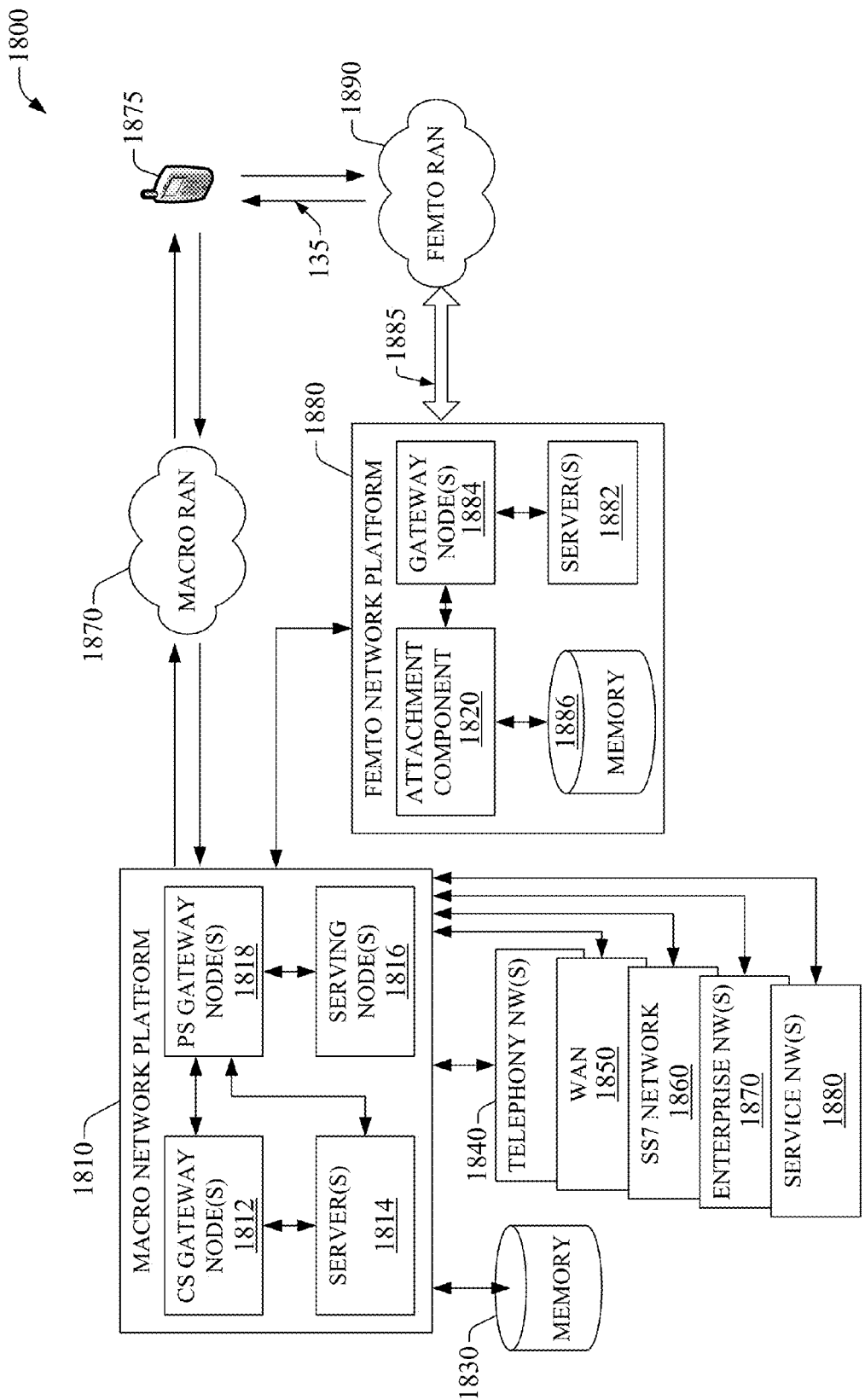
FIG. 18 illustrates example macro and femto wireless network environments that operate in accordance with the various aspects detailed herein.

With respect to FIG. 18, wireless communication environment 1800 includes two wireless network platforms: (i) A macro network platform 1810 which serves, or facilitates communication with user equipment 1875 (e.g., mobile 120$_A$) via a macro radio access network (RAN) 1870. It should be appreciated that in cellular wireless technologies (e.g., 3GPP UMTS, HSPA, 3GPP LTE, 3GPP2 UMB), macro network platform 1810 is embodied in a Core Network. (ii) A femto network platform 1880, which can provide communication with UE 1875 through a femto RAN 1890, which is linked to the femto network platform 1880 via backhaul pipe(s) 1885 (e.g., backhaul link(s) 140). It should be appreciated that macro network platform 1810 typically hands off UE 1875 to femto network platform 1810 once UE 1875 attaches (e.g., through macro-to-femto handover) to femto RAN 1890, which includes a set of deployed femto APs (e.g., femto AP 130) that can operate in accordance with aspects described herein.

It is noted that RAN includes base station(s), or access point(s), and its associated electronic circuitry and deployment site(s), in addition to a wireless radio link operated in accordance with the base station(s). Accordingly, macro RAN 1870 can comprise various coverage cells like cell 105, while femto RAN 1890 can comprise multiple femto cell access points such as femto AP 130. Deployment density in femto RAN 1890 is substantially higher than in macro RAN 1870.

Generally, both macro and femto network platforms 1810 and 1880 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject embodiments, macro network platform 1810 includes CS gateway node(s) 1812 which can interface CS traffic received from legacy networks like telephony network(s) 1840 (e.g., public switched telephone network (PSTN), or public land mobile network (PLMN)) or a SS7 network 1860. Circuit switched gateway 1812 can authorize and authenticate traffic (e.g., voice) arising from such networks. Additionally, CS gateway 1812 can access mobility, or roaming, data generated through SS7 network 1860; for instance, mobility data stored in a VLR, which can reside in memory 1830. Moreover, CS gateway node(s) 1812 interfaces CS-based traffic and signaling and gateway node(s) 1818. As an example, in a 3GPP UMTS network, PS gateway node(s) 1818 can be embodied in gateway GPRS support node(s) (GGSN).

In addition to receiving and processing CS-switched traffic and signaling, PS gateway node(s) 1818 can authorize and authenticate PS-based data sessions with served (e.g., through macro RAN) wireless devices. Data sessions can include traffic exchange with networks external to the macro network platform 1810, like wide area network(s) (WANs) 1850, enterprise networks (NW(s)) 1870 (e.g., enhanced 911), or service NW(s) 1880 like IP multimedia subsystem (IMS); it should be appreciated that local area network(s) (LANs), which may be a part of enterprise NW(s), can also be interfaced with macro network platform 1810 through PS gateway node(s) 1818. Packet-switched gateway node(s) 18 generates packet data contexts when a data session is established. To that end, in an aspect, PS gateway node(s) 1818 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 1814. It is to be noted that in 3GPP UMTS network(s), PS gateway node(s) 1818 (e.g., GGSN) and tunnel interface (e.g., TTG) comprise a packet data gateway (PDG).

Macro network platform 1810 also includes serving node(s) 1816 that convey the various packetized flows of information, or data streams, received through PS gateway node(s) 1818. As an example, in a 3GPP UMTS network, serving node(s) can be embodied in serving GPRS support node(s) (SGSN).

As indicated above, server(s) 1814 in macro network platform 1810 can execute numerous applications (e.g., location services, online gaming, wireless banking, wireless device management . . . ) that generate multiple disparate packetized data streams or flows, and manage (e.g., schedule, queue, format . . . ) such flows. Such application(s), for example can include add-on features to standard services provided by macro network platform 1810. Data streams can be conveyed to PS gateway node(s) 1818 for authorization/ authentication and initiation of a data session, and to serving node(s) 1816 for communication thereafter. Server(s) 1814 can also effect security (e.g., implement one or more firewalls) of macro network platform 1810 to ensure network's operation and data integrity in addition to authorization and authentication procedures that CS gateway node(s) 1812 and PS gateway node(s) 1818 can enact. Moreover, server(s) 1814 can provision services from external network(s), e.g., WAN 1850, or Global Positioning System (GPS) network(s), which can be a part of enterprise NW(s) 1880. It is to be noted that server(s) 1814 can include one or more processor configured to confer at least in part the functionality of macro network platform 1810. To that end, the one or more processor can execute code instructions stored in memory 1830, for example.

In example wireless environment 1800, memory 1830 stores information related to operation of macro network platform 1810. Information can include business data associated with subscribers; market plans and strategies, e.g., promotional campaigns, business partnerships; operational data for mobile devices served through macro network platform; service and privacy policies; end-user service logs for law enforcement; and so forth. Memory 1830 can also store information from at least one of telephony network(s) 1840, WAN 1850, SS7 network 1860, enterprise NW(s) 1870, or service NW(s) 1880.

Regarding femto network platform 1880, it includes a femto gateway node(s) 1884, which have substantially the same functionality as PS gateway node(s) 1818. Additionally, femto gateway node(s) 1884 can also include substantially all functionality of serving node(s) 1816. Disparate gateway node(s) 1884 can control or operate disparate sets of deployed femto APs, which can be a part of femto RAN 1890. In an aspect of the subject embodiments, femto gateway node(s) 1884 can aggregate operational data received from deployed femto APs. Moreover, femto gateway node(s) 1884, can convey received attachment signaling to attachment component 1820. It should be appreciated that while attachment component is illustrated as external to gateway node(s) 1884, attachment component 1820 can be an integral part of gateway node(s) 1884. Various interface components detailed supra in accordance with various aspects can be used to interact with the aforementioned nodes.

Attachment component 1820 can facilitate macro-to-femto and femto-to-macro handover with attachment to a femto AP (e.g., femto AP 130) dictated in accordance to a white list (e.g., white list(s) 220) and/or a white list profile (e.g., white list profile(s) 222). In an aspect, attachment component 1820 can include a determination of whether a white list resides within femto AP and whether a mobile station that is attempting attachment is whitelisted as described in the subject embodiments. It is noted, in an aspect, that when a whitelisted mobile station is allowed to attach to the femto AP, attachment component 1820 can establish femto service in accordance with privileges, or access logic, configured in a white list profile (e.g., white list profile(s) 222).

Memory 1886 can retain additional information relevant to operation of the various components of femto network platform 1880. For example operational information that can be stored in memory 1886 can comprise, but is not limited to, subscriber intelligence; contracted services; maintenance and service records; femto cell configuration (e.g., devices served through femto RAN 1890; authorized subscribers associated with one or more deployed femto APs); service policies and specifications; privacy policies; add-on features; so forth.

Server(s) 1882 have substantially the same functionality as described in connection with server(s) 1814. In an aspect, server(s) 1882 can execute multiple application(s) that provide service (e.g., voice and data) to wireless devices served through femto RAN 1890. Server(s) 1882 can also provide security features to femto network platform. In addition, server(s) 1882 can manage (e.g., schedule, queue, format . . . ) substantially all packetized flows (e.g., IP-based, frame relay-based, ATM-based) it generates in addition to data received from macro network platform 1810. Furthermore, server(s) 1882 can effect provisioning of femto cell service, and effect operations and maintenance. It is to be noted that server(s) 1882 can embody provisioning server 345, and can populate white list(s) and white list profile(s) in accordance with aspects described herein. It is to be noted that server(s) 1882 can include one or more processors configured to provide at least in part the functionality of femto network platform 1880. To that end, the one or more processors can execute code instructions stored in memory 1886, for example.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," "data storage," "database," and substantially any other information storage component relevant to operation and functionality of a component, refer to "memory components," or entities embodied in a "memory" or components comprising the memory. For example, information relevant to operation of various components described in the disclosed subject matter, and that can be stored in a memory, can comprise, but is not limited to comprising, subscriber information; femto cell configuration (e.g., devices served by a femto AP; access control lists, or white lists) or service policies and specifications; privacy policies; and so forth. It will be appreciated that the memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Various aspects or features described herein may be implemented as a method, apparatus, or article of manufacture using standard programming and/or engineering techniques. Implementation(s) that include software or firmware can be implemented at least in part through program modules stored in a memory and executed by a processor. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ).

What has been described above includes examples of systems and methods that provide advantages of the subject embodiments. It is, of course, not possible to describe every conceivable combination of components or methodologies for purposes of describing the claimed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A network device, comprising:
a processor; and
a memory that stores executable instructions that, when executed by the processor, facilitate performance of operations, comprising:
communicating with a first femto access point device associated with first account data indicative of a first subscriber to a network service, wherein the first femto access point device comprises first access control data comprising first user equipment identity data representing a first user equipment device that is allowed to access the network service via the first femto access point device;
determining that the first user equipment device is associated with second account data indicative of a second subscriber;
determining that the second account data is associated with a second femto access point device; and
transmitting, to a first receiving device associated with the first account data, first adding data comprising request data indicative of a request to authorize adding second user equipment identity data representing a second user equipment device associated with the first account data to second access control data associated with the second femto access point device.

2. The network device of claim 1, wherein the first receiving device is the second user equipment device and the first adding data is transmitted via a text message.

3. The network device of claim 1, wherein the operations further comprise:
in response to the transmitting the first adding data, receiving response data that indicates an authorization to add the second user equipment data to the second access control data.

4. The network device of claim 3, wherein the operations further comprise:
in response to the receiving the response data, transmitting, to a second receiving device associated with the second account data, request data comprising a request to add the second user equipment identity data to the second access control data.

5. The network device of claim 4, wherein the response data comprises an indication that the first femto access point device allows the first user equipment device to access the network service.

6. The network device of claim 4, wherein the second receiving device is the first user equipment device and the request data is transmitted via a text message.

7. The network device of claim 4, wherein the first access control data comprises third user equipment identity data representing a third user equipment device associated with third account data indicative of a third subscriber.

8. The network device of claim 7, wherein the operations further comprise:
transmitting to the second receiving device, second adding data comprising another request to add the third user equipment identity data to the second access control data.

9. The network device of claim 1, wherein the determining that the first user equipment device is associated with the second account data is in response to a provisioning procedure related to configuring the first access control data.

10. The network device of claim 1, wherein the determining that the second account data is associated with the second femto access point device is in response to a provisioning procedure related to configuring the second femto access point device to access a second network service.

11. The network device of claim 1, wherein the determining that the second account data is associated with the second femto access point device is in response to a provisioning procedure related to configuring the second access control data.

12. A method, comprising:
in response to a communication with a first femto access point device associated with first account data indicative of a first subscriber to a network service, determining, by a system comprising a processor, a first user equipment device that is associated with second account data indicative of a second subscriber, wherein the first femto access point device stores first access control data comprising first user equipment identity data representing the first user equipment device that is authorized to utilize the network service via the first femto access point device;
determining, by the system, that the second account data is associated with a second femto access point device; and
communicating, by the system, a first request to a first receiving device associated with the first account data, wherein the first request comprises a request to authorize adding second user equipment identity data representing a second user equipment device associated with the first account data to second access control data associated with the second femto access point device.

13. The method of claim 12, further comprising:
receiving, by the system, response data that indicates a consent to add the second user equipment data to the second access control data.

14. The method of claim 13, further comprising:
in response to the receiving the response data, transmitting, by the system, information representing a second request to a second receiving device associated with the second account data, wherein the second request comprises a request to add the second user equipment identity data to the second access control data.

15. The method of claim 12, wherein the determining that the second account data is associated with the second femto access point device comprises determining that the second account data is associated with the second femto access point device in response to a provisioning procedure related to configuring the second access control data.

16. The method of claim 12, wherein the network service is a first network service and the determining that the second account data is associated with the second femto access point device comprises determining that the second account data is associated with the second femto access point device in response to a provisioning procedure related to configuring the second femto access point device to access a second network service.

17. A non-transitory machine-readable storage medium, comprising executable instructions that, when executed by a processor, facilitate performance of operations, comprising:
in response to a communication with a first femto access point device related to first account data indicative of a first subscriber to a network service, wherein the first femto access point device stores a first access control data structure comprising first user equipment identity data representing a first user equipment device that is authorized to utilize the network service via the first femto access point device, determining the first user equipment device is associated with second account data indicative of a second subscriber;
determining that the second account data is associated with a second femto access point device; and
sending, to a first receiving device associated with the first account data, a first request to authorize adding second user equipment identity data representing a second user equipment device associated with the first account data to a second access control data structure associated with the second femto access point device.

18. The non-transitory machine-readable storage medium of claim 17, wherein the operations further comprise receiving, in response to the sending, response data that indicates authorized consent to add the second user equipment data to the second access control data structure.

19. The non-transitory machine-readable storage medium of claim 18, wherein the operations further comprise, in response to the receiving the response data, sending to a second receiving device associated with the second account data, a second request to add the second user equipment identity data to the second access control data structure.

20. The non-transitory machine-readable storage medium of claim 17, wherein the determining that the second account data is associated with the second femto access point device is in response to a provisioning procedure related to configuring the second femto access point device to access a second network service.

* * * * *